(12) United States Patent
Silvestro

(10) Patent No.: US 9,446,222 B2
(45) Date of Patent: Sep. 20, 2016

(54) CATHETER ASSEMBLIES AND METHODS FOR STABILIZING A CATHETER ASSEMBLY WITHIN A SUBINTIMAL SPACE

(71) Applicant: Invatec S.p.A., Roncadelle (IT)

(72) Inventor: Claudio Silvestro, Monza e Brianza (IT)

(73) Assignee: Invatec S.P.A., Roncadelle (IT)

( * ) Notice: Subject to any disclaimer, the term of this patent is extended or adjusted under 35 U.S.C. 154(b) by 172 days.

(21) Appl. No.: 14/197,803

(22) Filed: Mar. 5, 2014

(65) Prior Publication Data

US 2015/0250991 A1    Sep. 10, 2015

(51) Int. Cl.
| | |
|---|---|
| *A61M 29/00* | (2006.01) |
| *A61M 25/10* | (2013.01) |
| *A61M 29/02* | (2006.01) |
| *A61B 17/22* | (2006.01) |
| *A61M 25/02* | (2006.01) |

(Continued)

(52) U.S. Cl.
CPC ......... *A61M 25/1002* (2013.01); *A61M 29/02* (2013.01); *A61B 17/3478* (2013.01); *A61B 2017/00331* (2013.01); *A61B 2017/22095* (2013.01); *A61M 2025/0293* (2013.01); *A61M 2025/1084* (2013.01); *A61M 2025/1097* (2013.01)

(58) Field of Classification Search
CPC ............ A61B 2017/22095; A61B 17/320758; A61B 2017/22094; A61B 17/3207; A61M 2025/0197; A61M 25/1002; A61M 2025/018; A61M 2025/1013; A61M 2025/1084; A61M 25/007; A61M 25/0082; A61M 25/104; A61M 2025/0293; A61M 2025/1004; A61M 25/0032; A61M 25/0152; A61M 25/0194; A61M 25/10; A61M 25/1009; A61M 2025/109
USPC ............ 606/159, 191, 194, 198; 604/103.06, 604/504
See application file for complete search history.

(56) References Cited

U.S. PATENT DOCUMENTS

| | | |
|---|---|---|
| 3,568,659 A | 3/1971 | Karnegis |
| 4,552,554 A | 11/1985 | Gould et al. |
| 4,774,949 A | 10/1988 | Fogarty |

(Continued)

FOREIGN PATENT DOCUMENTS

| | | |
|---|---|---|
| EP | 1765193 | 10/2012 |
| WO | WO2008120209 | 10/2008 |

(Continued)

OTHER PUBLICATIONS

U.S. Appl. No. 13/952,973, filed Jul. 29, 2013, Silvestro.

(Continued)

*Primary Examiner* — Katherine M Shi

(57) ABSTRACT

Catheter assemblies include a stabilization mechanism disposed at a distal end of the catheter assembly for stabilizing the catheter assembly within a subintimal space. The stabilization mechanism includes a self-expanding support structure that is slidably positionable within an inflatable balloon. The catheter assemblies include an outer shaft which has the balloon at a distal end thereof and an inner shaft which has the support structure mounted on a distal end thereof. The inner shaft is slidably disposed within a lumen of the outer shaft and has a first configuration in which the support structure is held in a compressed state within the outer shaft and a second configuration in which the support structure is permitted to return to an expanded state within the inflatable balloon. In the expanded state, the stabilization mechanism has a flattened laterally-extending profile.

14 Claims, 19 Drawing Sheets

(51) Int. Cl.
   *A61B 17/34*    (2006.01)
   *A61B 17/00*    (2006.01)

(56) References Cited

U.S. PATENT DOCUMENTS

| | | |
|---|---|---|
| 5,002,532 A | 3/1991 | Graiser et al. |
| 5,460,608 A | 10/1995 | Lodin et al. |
| 5,569,184 A | 10/1996 | Crocker et al. |
| 5,667,493 A | 9/1997 | Janacek |
| 5,707,389 A | 1/1998 | Louw et al. |
| 5,830,222 A | 11/1998 | Makower |
| 5,916,194 A | 6/1999 | Jacobsen et al. |
| 5,947,994 A | 9/1999 | Louw et al. |
| 6,068,638 A | 5/2000 | Makower |
| 6,071,292 A | 6/2000 | Makower et al. |
| 6,081,738 A | 6/2000 | Hinohara et al. |
| 6,159,225 A | 12/2000 | Makower |
| 6,178,968 B1 | 1/2001 | Louw et al. |
| 6,190,353 B1 | 2/2001 | Makower et al. |
| 6,203,524 B1 | 3/2001 | Burney et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,231,563 B1 | 5/2001 | White et al. |
| 6,231,587 B1 | 5/2001 | Makower et al. |
| 6,235,000 B1 | 5/2001 | Milo et al. |
| 6,261,260 B1 | 7/2001 | Maki et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,355,027 B1 | 3/2002 | Le et al. |
| 6,375,615 B1 | 4/2002 | Makower et al. |
| 6,379,319 B1 | 4/2002 | Garibotto et al. |
| 6,432,127 B1 | 8/2002 | Kim et al. |
| 6,447,477 B2 | 9/2002 | Burney et al. |
| 6,458,098 B1 | 10/2002 | Kanesaka |
| 6,508,824 B1 | 1/2003 | Flaherty et al. |
| 6,511,458 B2 | 1/2003 | Milo et al. |
| 6,514,217 B1 | 2/2003 | Selmon et al. |
| 6,514,228 B1 | 2/2003 | Hamilton et al. |
| 6,544,230 B1 | 4/2003 | Flaherty et al. |
| 6,579,311 B1 | 6/2003 | Makower |
| 6,602,241 B2 | 8/2003 | Makower et al. |
| 6,655,386 B1 | 12/2003 | Makower et al. |
| 6,669,709 B1 | 12/2003 | Cohn et al. |
| 6,709,444 B1 | 3/2004 | Makower |
| 6,719,725 B2 | 4/2004 | Milo et al. |
| 6,726,677 B1 | 4/2004 | Makower et al. |
| 6,746,464 B1 | 6/2004 | Makower et al. |
| 7,004,173 B2 | 2/2006 | Sparks et al. |
| 7,059,330 B1 | 6/2006 | Makower et al. |
| 7,066,914 B2 | 6/2006 | Andersen |
| 7,141,041 B2 | 11/2006 | Seward |
| 7,179,270 B2 | 2/2007 | Makower et al. |
| 7,316,655 B2 | 1/2008 | Garibotto et al. |
| 7,357,794 B2 | 4/2008 | Makower et al. |
| 7,534,223 B2 | 5/2009 | Boutilette et al. |
| 7,606,615 B2 | 10/2009 | Makower et al. |
| 7,637,870 B2 | 12/2009 | Flaherty et al. |
| 7,729,738 B2 | 6/2010 | Flaherty et al. |
| 7,833,197 B2 | 11/2010 | Boutilette |
| 7,854,727 B2 | 12/2010 | Belsley |
| RE42,049 E | 1/2011 | Schroeder et al. |
| 7,878,986 B2 | 2/2011 | Jen et al. |
| 7,938,819 B2 | 5/2011 | Kugler et al. |
| 8,083,727 B2 | 12/2011 | Kugler et al. |
| 8,172,863 B2 | 5/2012 | Robinson et al. |
| 8,202,246 B2 | 6/2012 | Kugler et al. |
| 8,221,357 B2 | 7/2012 | Boutillette |
| 8,226,566 B2 | 7/2012 | Nita |
| 8,241,311 B2 | 8/2012 | Ward et al. |
| 8,257,382 B2 | 9/2012 | Rottenberg et al. |
| 8,323,261 B2 | 12/2012 | Kugler et al. |
| 8,337,425 B2 | 12/2012 | Olson et al. |
| 8,388,876 B2 | 3/2013 | Boutilette et al. |
| 8,460,254 B2 | 6/2013 | Belsley |
| 8,486,022 B2 | 7/2013 | Ludwig et al. |
| 8,496,679 B2 | 7/2013 | Robinson et al. |
| 8,512,310 B2 | 8/2013 | Kugler et al. |
| 8,535,245 B2 | 9/2013 | Jen et al. |
| 8,556,857 B2 | 10/2013 | Boutillette |
| 2001/0000041 A1 | 3/2001 | Selmon et al. |
| 2002/0072706 A1 | 6/2002 | Hiblar et al. |
| 2003/0163154 A1 | 8/2003 | Miyata et al. |
| 2004/0167554 A1 | 8/2004 | Simpson et al. |
| 2005/0021003 A1 | 1/2005 | Caso et al. |
| 2005/0171478 A1 | 8/2005 | Selmon et al. |
| 2006/0074442 A1 | 4/2006 | Noriega et al. |
| 2006/0094930 A1 | 5/2006 | Sparks et al. |
| 2006/0276749 A1 | 12/2006 | Selmon et al. |
| 2008/0125748 A1 | 5/2008 | Patel |
| 2008/0147000 A1 | 6/2008 | Seibel et al. |
| 2008/0249464 A1 | 10/2008 | Spencer et al. |
| 2009/0124899 A1 | 5/2009 | Jacobs et al. |
| 2010/0010522 A1 | 1/2010 | Shturman |
| 2010/0063534 A1 | 3/2010 | Kugler et al. |
| 2011/0144677 A1 | 6/2011 | Ward et al. |
| 2011/0276079 A1 | 11/2011 | Kugler et al. |
| 2012/0053485 A1 | 3/2012 | Bloom |
| 2012/0095485 A1 | 4/2012 | Cully et al. |
| 2012/0283571 A1 | 11/2012 | Nita |
| 2012/0283761 A1 | 11/2012 | Rosenthal et al. |
| 2012/0323251 A1 | 12/2012 | Kugler et al. |
| 2012/0323269 A1 | 12/2012 | Rottenberg et al. |
| 2013/0006167 A1 | 1/2013 | Alvarez |
| 2013/0006173 A1 | 1/2013 | Alvarez et al. |
| 2013/0006282 A1 | 1/2013 | Wilkinson |
| 2013/0072957 A1 | 3/2013 | Anderson |
| 2013/0103070 A1 | 4/2013 | Kugler et al. |
| 2013/0116622 A1 | 5/2013 | Takagi |
| 2013/0158519 A1 | 6/2013 | Boutilette et al. |
| 2013/0245430 A1 | 9/2013 | Selmon et al. |
| 2013/0296907 A1 | 11/2013 | Robinson et al. |
| 2013/0304108 A1 | 11/2013 | Weber et al. |
| 2013/0310868 A1 | 11/2013 | Kugler et al. |
| 2013/0317528 A1 | 11/2013 | Anderson et al. |

FOREIGN PATENT DOCUMENTS

| | | |
|---|---|---|
| WO | WO2009144561 | 12/2009 |
| WO | WO2013003757 | 1/2013 |
| WO | WO2013164825 | 11/2013 |

OTHER PUBLICATIONS

U.S. Appl. No. 13/952,981, filed Jul. 29, 2013, Silvestro.
U.S. Appl. No. 14/460,048, filed Aug. 14, 2014, Guala et al.
U.S. Appl. No. 14/058,444, filed Oct. 21, 2013, Silvestro.
Shin et al. "Limitations of the Outback LTD re-entry device in femoropopliteal chronic total occlusions." Journal of Vascular Surgery, vol. 53, 5; 2010.
A. Bolia "Subintimial Angioplasty, the Way Forward" Acta chir belg, 2004, 104, 547-554.
Karkos et al. "Subintimal Recanalization of the Femoropopliteal Segment to Promote Healing of an Ulcerated Below-Knee Amputation Stump" J Endovasc Ther 2006;13:420-423.
Glasby et al. "Subintimal Angioplasty" Review, pp. 12-16, 2008.
Bolia A. "Subintimal Angioplasty, Tips and Technique: How Long Can You Go?"

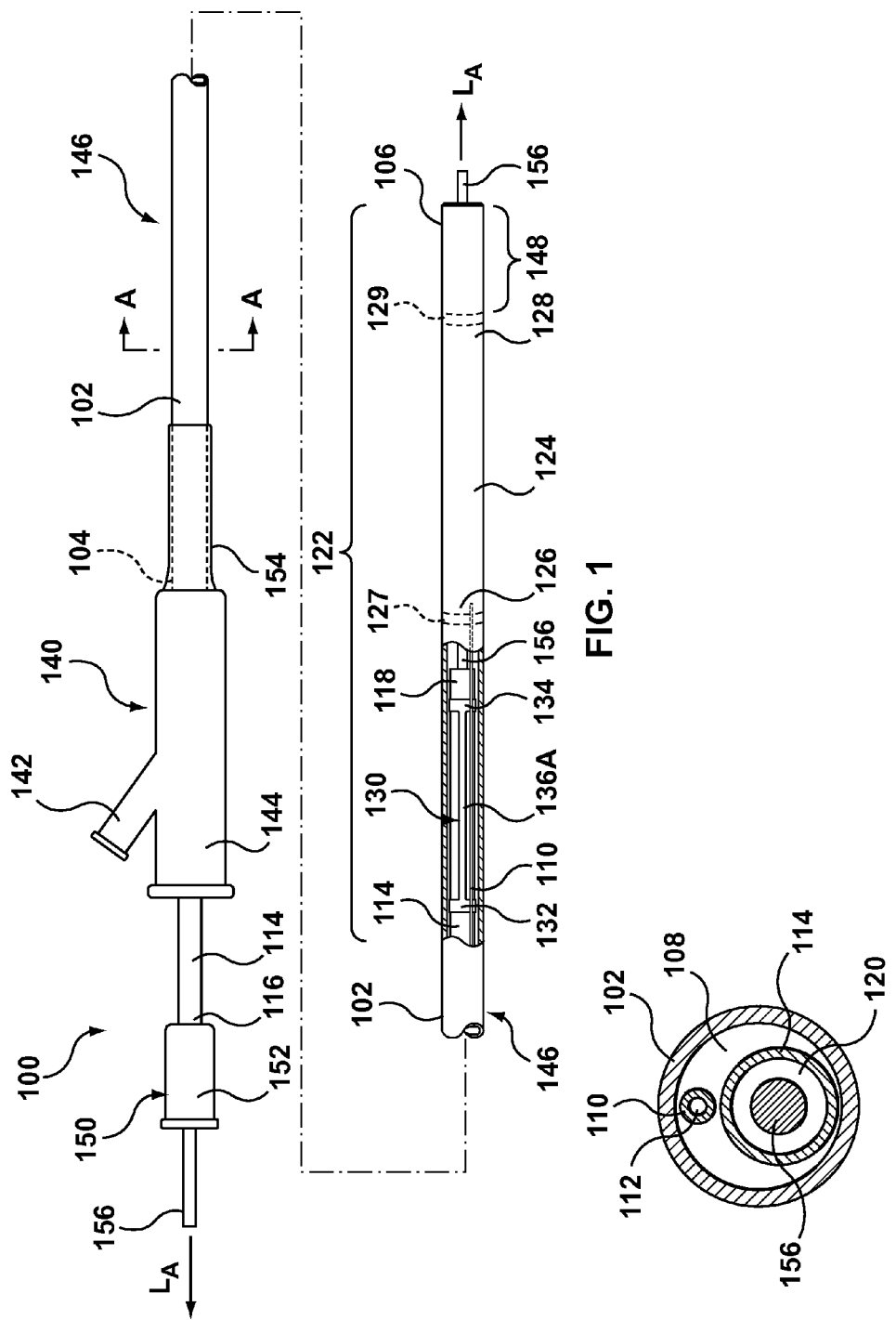

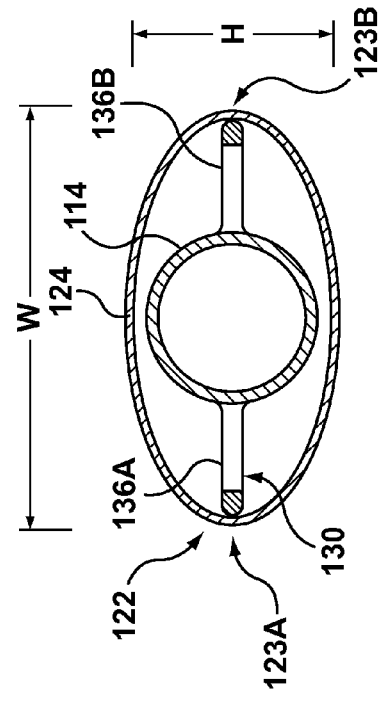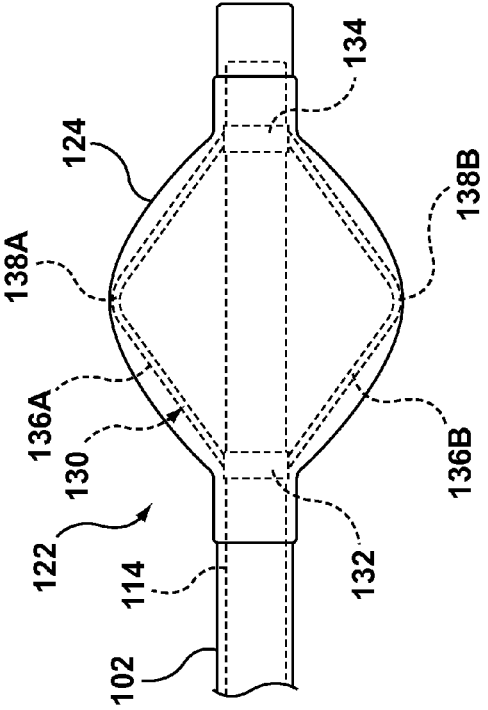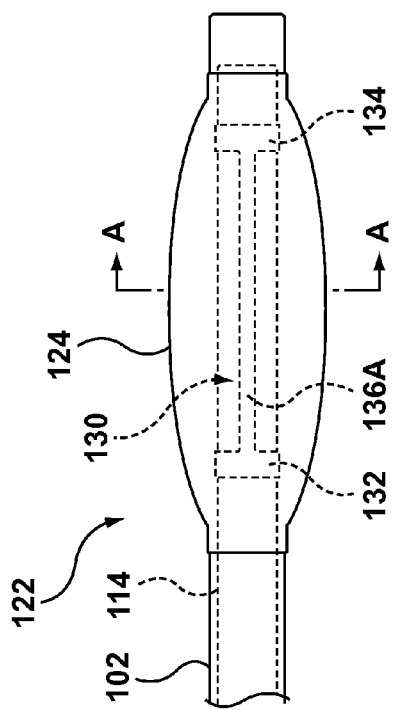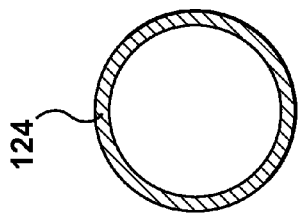

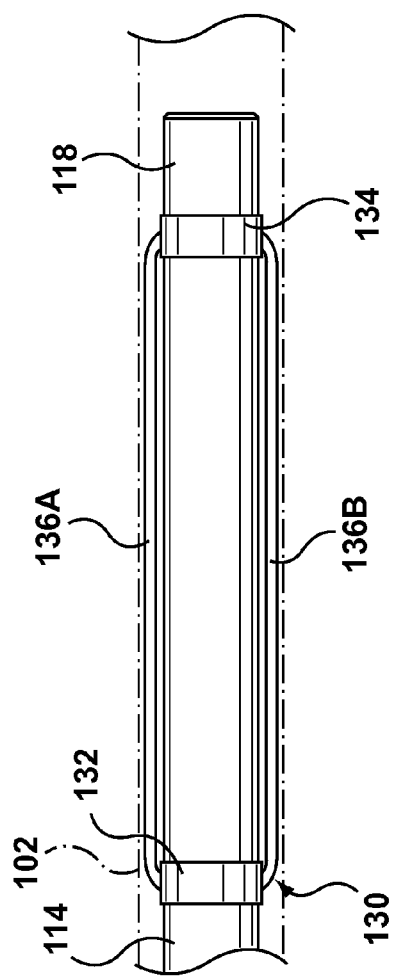
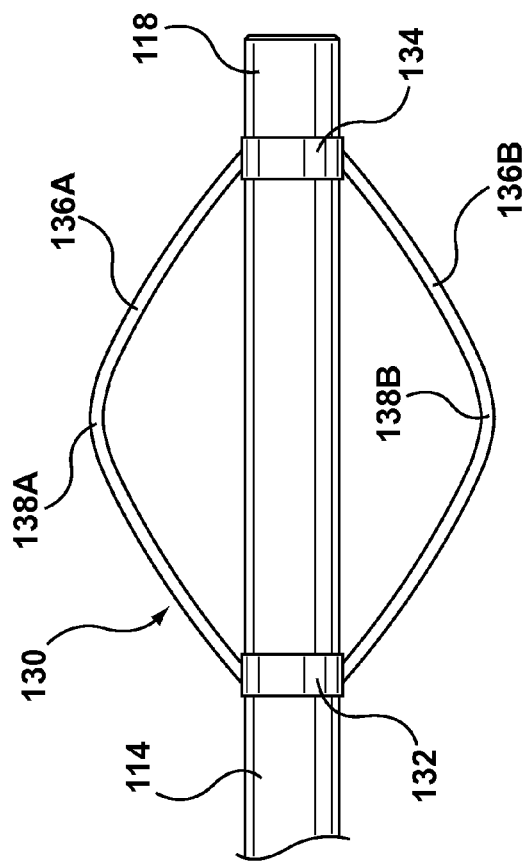
FIG. 6A
FIG. 6B

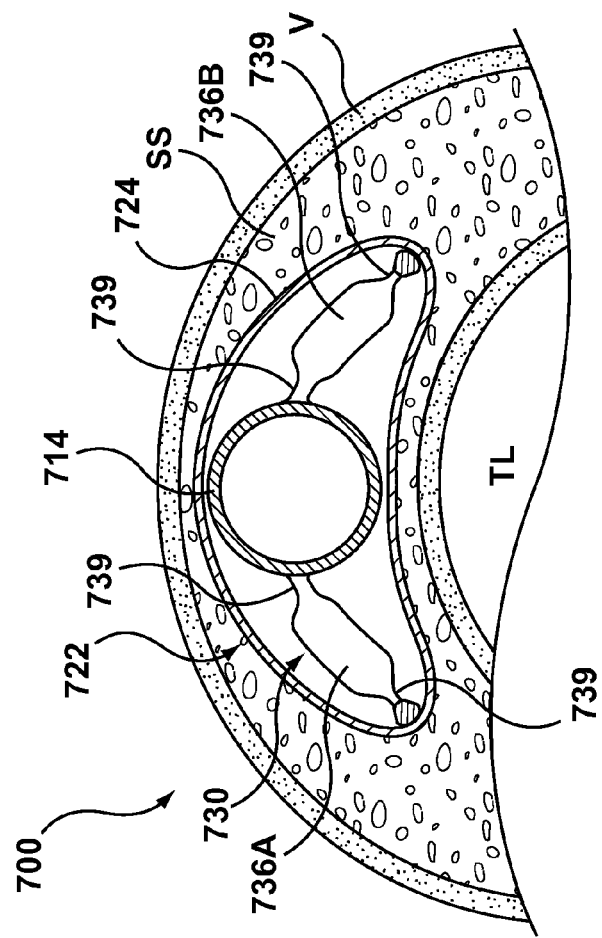
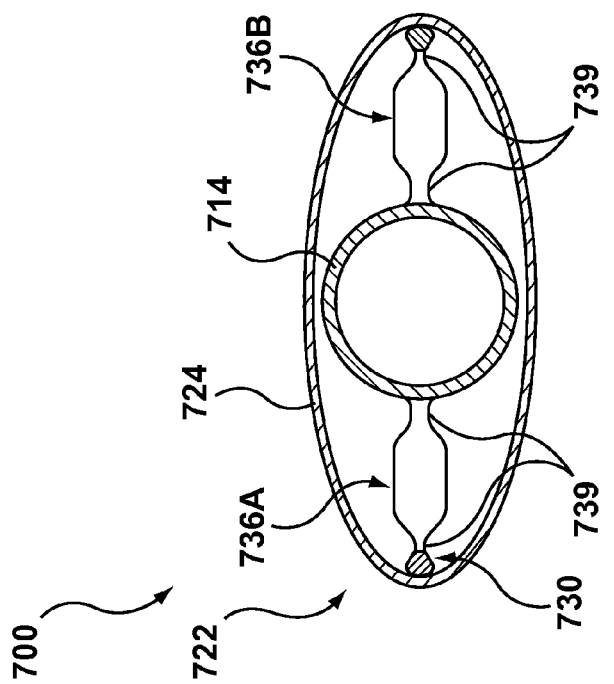
FIG. 8
FIG. 7

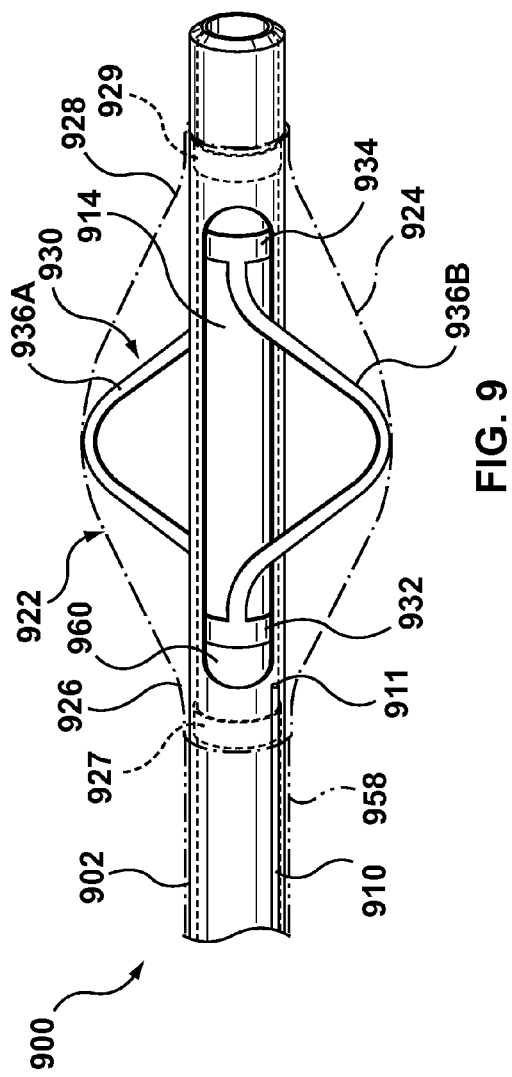
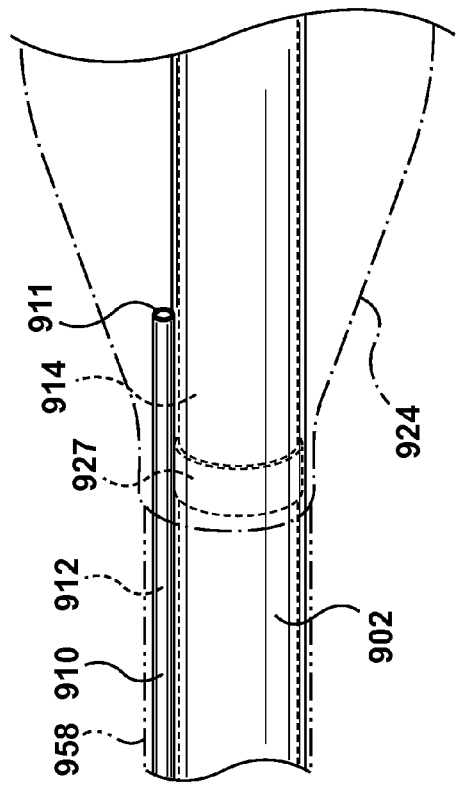
FIG. 9
FIG. 10

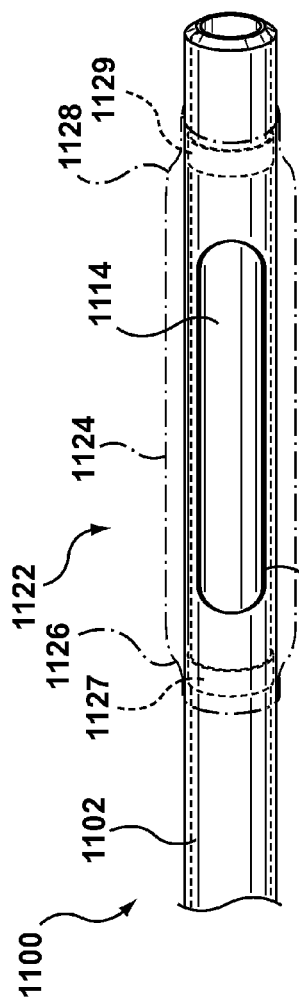
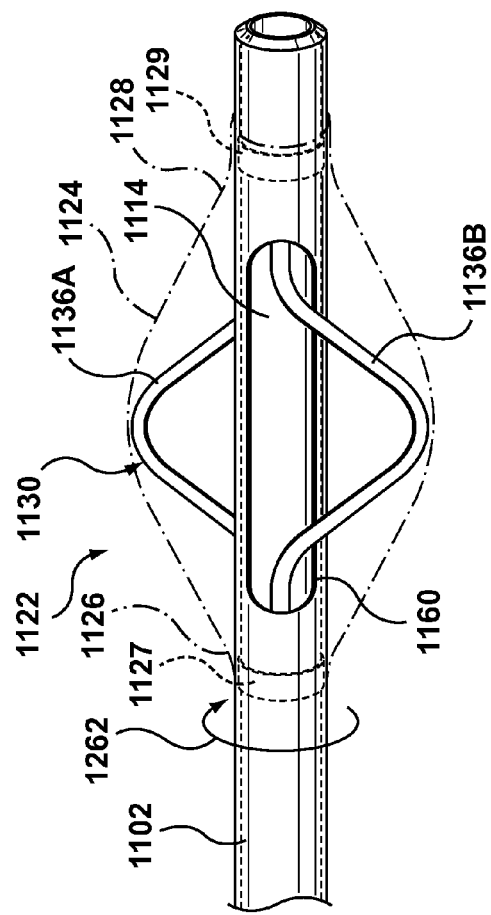
FIG. 11
FIG. 12

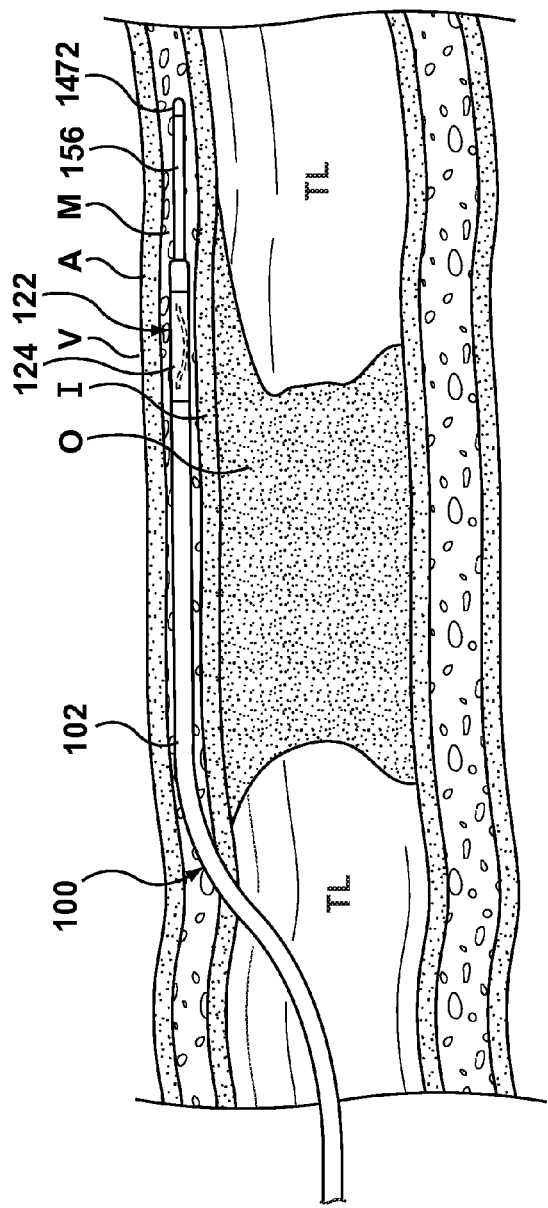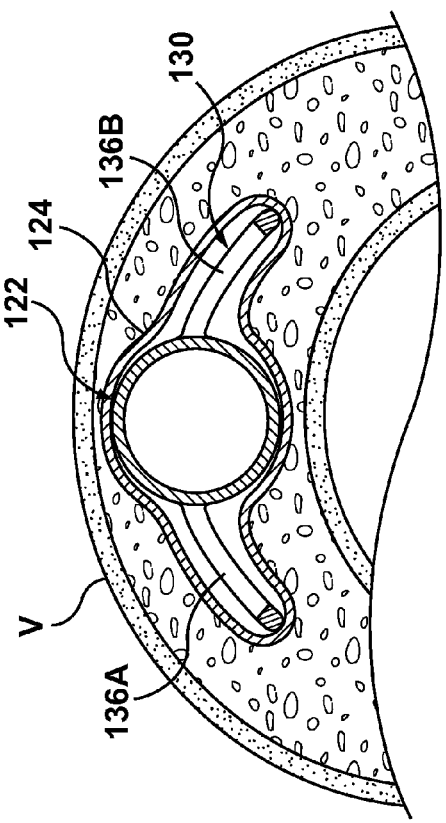

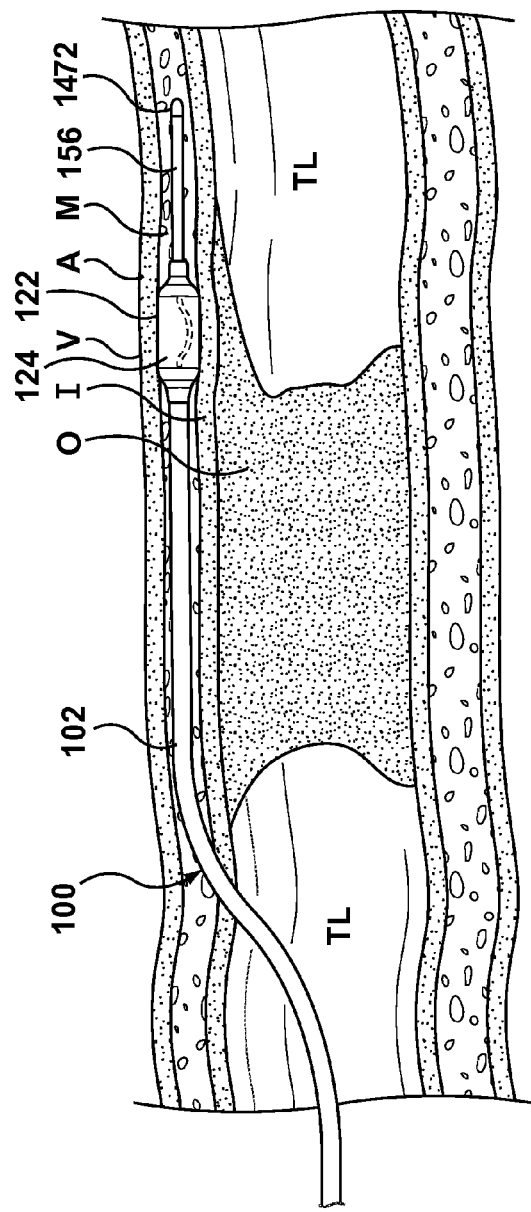
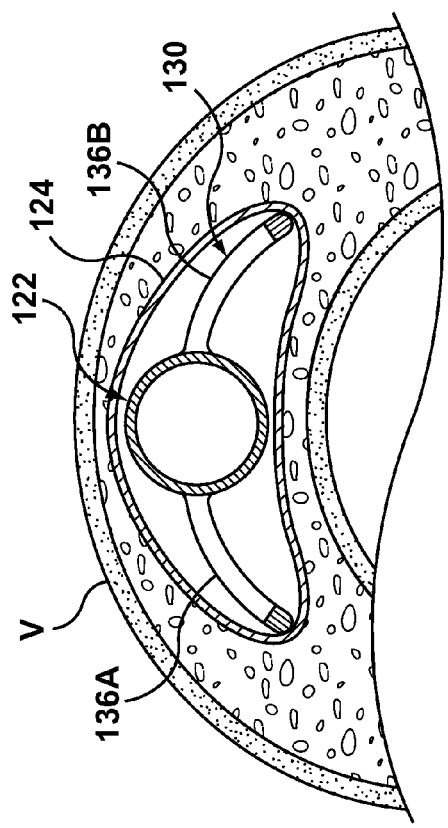
FIG. 17
FIG. 17A

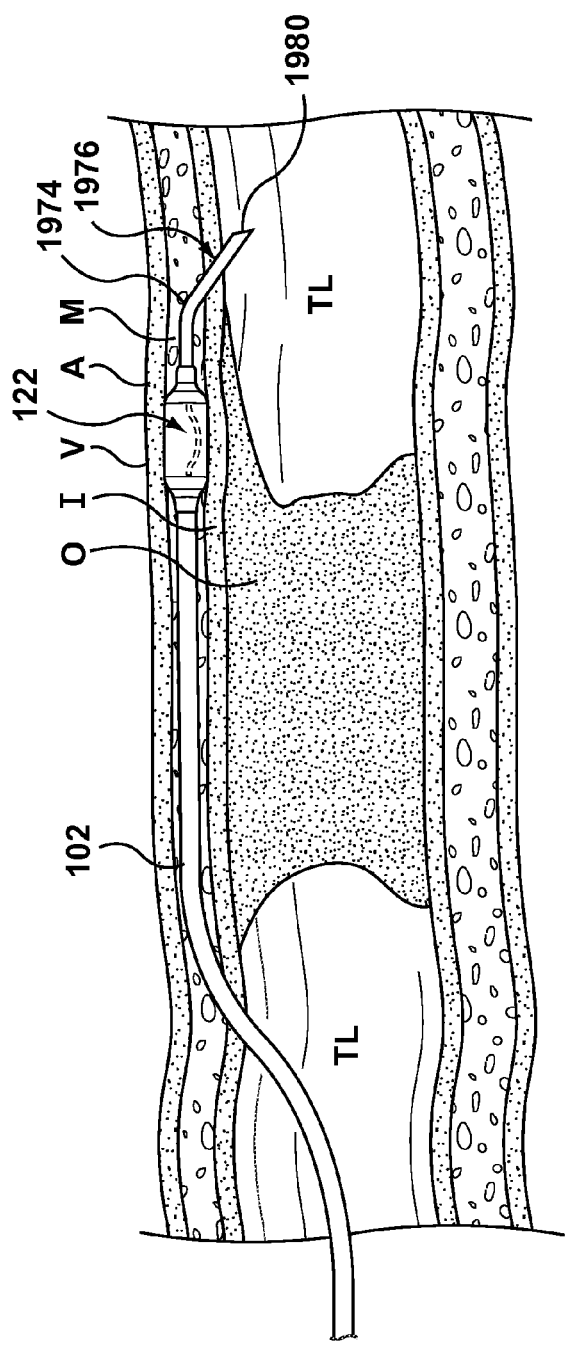
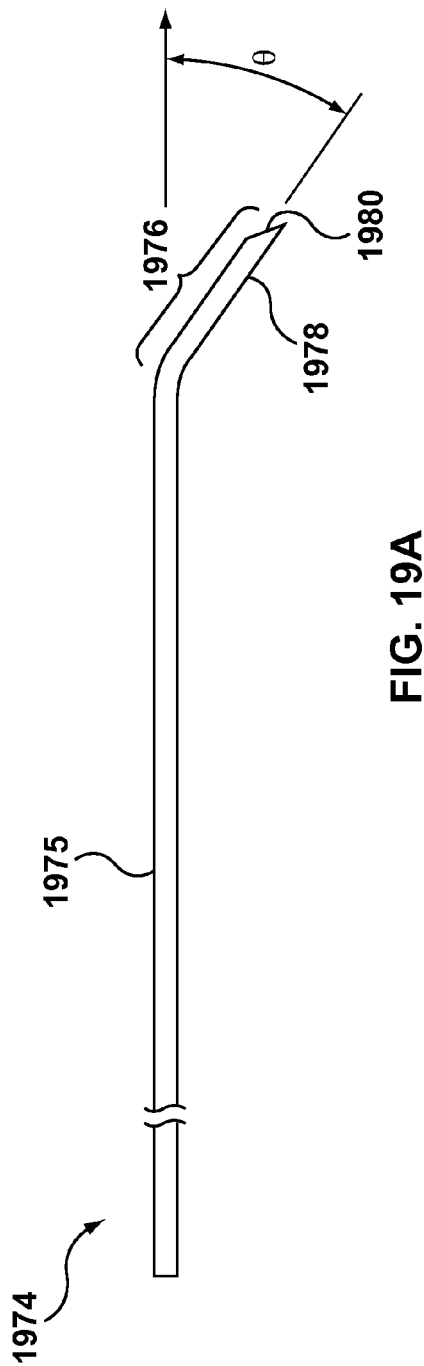
FIG. 19
FIG. 19A

CATHETER ASSEMBLIES AND METHODS FOR STABILIZING A CATHETER ASSEMBLY WITHIN A SUBINTIMAL SPACE

FIELD OF THE INVENTION

The invention relates generally to catheters and more particularly to catheter assemblies that provide stabilization within a subintimal space of a vessel wall.

BACKGROUND OF THE INVENTION

Cardiovascular disease, including atherosclerosis, is the leading cause of death in the United States. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel.

The anatomy of arteries varies widely from patient to patient. Often patient's arteries are irregularly shaped, highly tortuous and very narrow. The tortuous configuration of the arteries may present difficulties to a clinician in advancement of the balloon catheter to a treatment site. In addition, in some instances, the extent to which the lumen is narrowed at the treatment site is so severe that the lumen is completely or nearly completely obstructed, which may be described as a total occlusion. Total or near-total occlusions in arteries can prevent all or nearly all of the blood flow through the affected arteries. If the total or near total occlusion has been established for a long period of time, the lesion may be referred to as a chronic total occlusion or CTO. Chronic total occlusions can occur in coronary as well as peripheral arteries. Chronic total occlusions are often characterized by extensive plaque formation and typically include a fibrous cap surrounding softer plaque material. This fibrous cap may present a surface that is difficult to penetrate with a conventional medical guidewire.

A number of devices have been developed and/or used for the percutaneous interventional treatment of CTOs, such as stiffer guidewires, low-profile balloons, laser light emitting wires, atherectomy devices, drills, drug eluting stents, and re-entry catheters. The factor that is most determinative of whether the physician can successfully recanalize a CTO is the physician's ability to advance a suitable guidewire from a position within the true lumen of the artery that is proximal to the CTO lesion, across the CTO lesion, i.e., either through the lesion or around it, and then back into the true lumen of the artery at a location that is distal to the CTO lesion.

In some cases, such as where the artery is totally occluded by hard, calcified atherosclerotic plaque, the guidewire may tend to deviate to one side and penetrate through the intima of the artery, thereby creating a neo-lumen called a "subintimal space," i.e., a penetration space or tract formed within the wall of the artery between the intima and adventitia. In these cases, the distal end of the guidewire may be advanced to a position distal to the lesion but remains trapped within the subintimal tract. In such instances, it is then necessary to direct or steer the guidewire from the subintimal tract back into the true lumen of the artery at a location distal to the CTO lesion. The process of manipulating the guidewire to reenter the artery lumen is often difficult and various solutions have been proposed utilizing means for handling such a presentation.

For example, a number of catheter-based devices have been suggested for redirecting subintimally placed guidewires or other medical devices back into the true lumen of the artery. Included among these are a variety of catheters having laterally deployable elements i.e., pre-shaped needles or puncturing stylets. For example, a catheter system may utilize a penetrator or needle that exits through a side exit port of the catheter to puncture the intimal layer distal of the CTO to re-enter the true lumen of the vessel. A second guidewire is then passed through the laterally deployed needle and is advanced into the true lumen of the artery. In cases in which deployable elements such as pre-shaped needles or puncturing stylets are used, their efficacy is enhanced by the stability of the catheter system inside the subintimal space. In order to provide greater stability to the catheter system, an inflatable balloon may be utilized to anchor the system inside the subintimal space. A need in the art still exists for other medical devices or systems that consistently and reliably anchor a catheter system inside the subintimal space to enhance stability of the catheter system either before or after the deployment of the puncturing element.

BRIEF SUMMARY OF THE INVENTION

Embodiments hereof are directed to a catheter assembly including an outer shaft including an inflatable balloon disposed at a distal end thereof and an inner shaft including a self-expanding support structure mounted on a distal end thereof. The inner shaft is disposed within a lumen of the outer shaft such that the inner shaft is movable relative to the outer shaft. In a first configuration, the support structure is held in a radially compressed state within the outer shaft. In a second configuration, the support structure is permitted to return to an expanded state within the inflatable balloon such that the inflatable balloon has a flattened laterally-extending profile dictated by the support structure in the expanded state for anchoring the catheter assembly within the subintimal space.

Another embodiment hereof is directed to a catheter assembly that provides stabilization within a subintimal space including a stabilization mechanism disposed at a distal end of the catheter assembly. The stabilization mechanism includes a self-expanding support structure that is selectively positionable within an inflatable balloon. When the support structure is positioned within the balloon, the support structure returns to an expanded state and causes the balloon to have a flattened laterally-extending profile that corresponds to the geometry of the support structure therein for anchoring the catheter assembly within the subintimal space.

Embodiments hereof also relate to a method of stabilizing a catheter assembly within a subintimal space. In one such method, a distal end of the catheter assembly is tracked to a treatment site within the subintimal space with a self-expanding support structure held in a compressed state therein. The support structure is positioned within an inflatable balloon of the catheter assembly to permit the support structure to return to an expanded state within the balloon. The balloon is inflated around the support structure, wherein an inflated profile of the balloon corresponds to the geometry of the support structure therein.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a catheter assembly having a stabilization mechanism according to an embodiment hereof, with a portion thereof shown in section, wherein the stabilization mechanism is shown in a first or delivery state.

FIG. 1A is a cross-sectional view taken along line A-A of FIG. 1.

FIGS. 2 and 3 are side and top views, respectively, of a distal portion of the catheter assembly of FIG. 1, wherein the stabilization mechanism is shown in a second or deployed state.

FIG. 2A is a cross-sectional view taken along line A-A of FIG. 2.

FIG. 2B is a cross-sectional view of a balloon of the catheter assembly of FIG. 1, wherein the balloon is inflated without a support structure therein.

FIG. 6A is a top view of a distal portion of an inner shaft of the catheter assembly of FIG. 1, wherein the support structure is shown in a first or delivery state.

FIG. 6B is a top view of the distal portion of the inner shaft of the catheter assembly of FIG. 1 removed from the remainder of the catheter assembly, wherein the support structure is shown in a second or deployed state.

FIG. 7 is cross-sectional view of an inner shaft and support structure according to another embodiment hereof, wherein the support structure is shown in a second or deployed state.

FIG. 8 illustrates a cross-sectional view of a portion of the vessel of FIG. 4 with a catheter assembly of FIG. 7 deployed within the subintimal space.

FIG. 9 is a perspective view of a distal portion of a catheter assembly according to another embodiment hereof, wherein a stabilization mechanism of the catheter assembly is shown in a second or deployed state.

FIG. 10 is an enlarged view of a proximal end of a balloon of the stabilization mechanism of the catheter assembly of FIG. 9.

FIG. 11 is a perspective view of a distal portion of a catheter assembly according to another embodiment hereof, wherein a stabilization mechanism of the catheter assembly is shown in a first or delivery state.

FIG. 12 is a perspective view of the distal portion of the catheter assembly of FIG. 11, wherein the stabilization mechanism is shown in a second or deployed state.

FIGS. 14-24 illustrate the steps of utilizing the catheter assembly of FIG. 1 to bypass a chronic total occlusion according to an embodiment hereof.

DETAILED DESCRIPTION OF THE INVENTION

Figure 5:
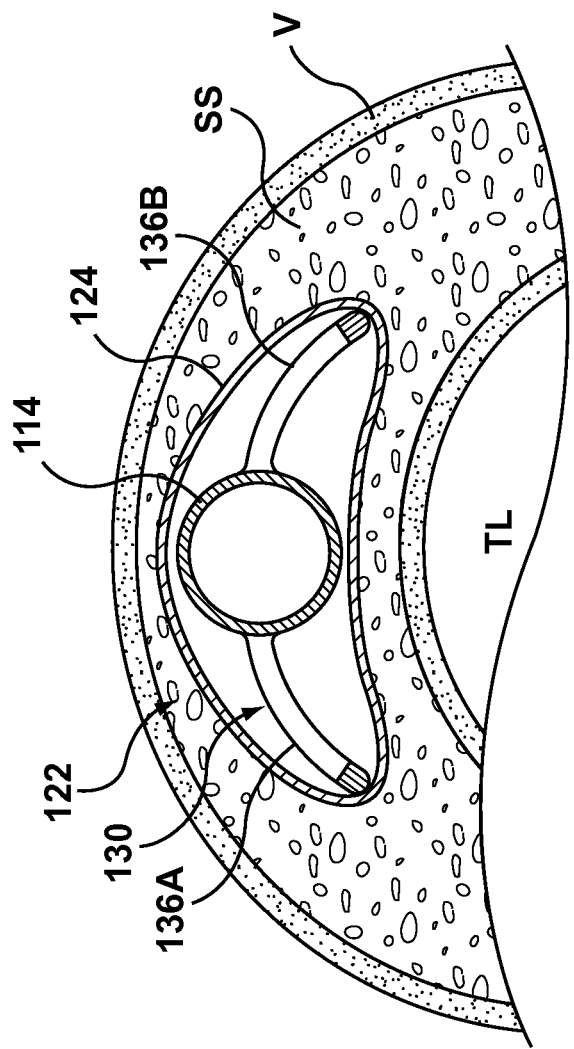
FIG. 5 illustrates a cross-sectional view of a portion of the vessel of FIG. 4 with the catheter assembly of FIG. 1 deployed within the subintimal space.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. The term "shape memory" is used in the following description with reference to a self-expanding support structure and is intended to convey that the structure is shaped or formed from a material that can be provided with a mechanical memory to return the structure from a straightened or compressed delivery state to an expanded or deployed state. Non-exhaustive exemplary materials that may be imparted with a shape memory include stainless steel, a pseudo-elastic metal such as a nickel titanium alloy or nitinol, a so-called super alloy, which may have a base metal of nickel, cobalt, chromium, or other metal, or a polymer having a shape memory such as but not limited to polyetheretherketone (PEEK). Shape memory may be imparted to a support structure by thermal treatment to achieve a spring temper in stainless steel, for example, or to set a mechanical memory in a susceptible metal alloy, such as nitinol.

The following detailed description is merely exemplary in nature and is not intended to limit the invention or the application and uses of the invention. Although the description of the invention is in the context of treatment of blood vessels such as peripheral or coronary arteries, the invention may also be used in any other body passageways where it is deemed useful. Further, although the description of the invention generally refers to a catheter assembly and method of bypassing a vessel blockage in a proximal-to-distal direction, i.e. antegrade or with the blood flow, the invention may be used equally well to bypass a vessel blockage in a distal-to-proximal direction, i.e. retrograde or against the blood flow if access is available from that direction. In other terms, the assembly and method described herein may be considered to bypass a vessel blockage from a near side of the blockage to a far side of the blockage. Additionally, the catheter assembly may be used for stabilization within a subintimal space in other procedures or methods and is not limited to methods of bypassing an occlusion. There is no intention to be bound by any expressed or implied theory presented in the preceding technical field, background, brief summary or the following detailed description.

Embodiments hereof relate to a catheter assembly 100 having a stabilization mechanism 122 for stabilizing or anchoring the catheter assembly within a subintimal space. Stabilization mechanism 122 includes a self-expanding support structure 130 that is slidably positionable within an inflatable balloon 124. Catheter assembly 100 includes an outer shaft 102 having inflatable balloon 124 at a distal end thereof and an inner shaft 114 having self-expanding support structure 130 mounted on a distal end portion thereof. Inner shaft 114 is slidably disposed within a continuous lumen 108 that is defined within outer shaft 102 from a proximal end 104 to a distal end 106 thereof.

In a first or delivery configuration of stabilization mechanism 122 shown in FIG. 1, self-expanding support structure 130 is held in a compressed state within outer shaft 102 proximal of balloon 124. When inner shaft 114 is longitudinally translated relative to outer shaft 102, stabilization mechanism 122 is placed in the second or deployed configuration of FIGS. 2 and 3, wherein support structure 130 and balloon 124 are longitudinally aligned as explained in more detail herein and support structure 130 is permitted to return to a laterally expanded state within balloon 124. The laterally expanded support structure dictates or constrains expansion of balloon 124 such that the balloon assumes a flattened, laterally-extending profile when in an inflated state as will be described in more detail herein. Accordingly, when in the second or deployed configuration, stabilization mechanism 122 may be described as having a flattened, non-circular profile for anchoring the catheter assembly within target anatomical space due to laterally expanded support structure 130 with balloon 124 inflated there around. Together, support structure 130 and balloon 124 function to stabilize or anchor a distal portion of catheter assembly 100 within a target anatomical space, so as to minimize any axial or rotational motion of the catheter assembly during further procedural steps. For example, catheter assembly 100 may be utilized as a re-entry catheter for bypassing a chronic total occlusion (CTO) or other occlusion. In such an example, as will be explained in more detail herein, stabilization mechanism 122 is utilized to anchor catheter assembly 100 within the subintimal space prior to, during, or after deployment of a needle component that is used to puncture a blood vessel wall to re-enter a true lumen of the blood vessel.

Inner shaft 114 is an elongate tubular or cylindrical element that is configured to be slidably disposed within lumen 108 of outer shaft 102. As used herein, "slidably" denotes back and forth movement in a longitudinal direction along a longitudinal axis $L_A$ of the catheter assembly 100. Inner shaft 114 defines at least one lumen 120 that extends from a proximal end 116 to a distal end 118 thereof. Proximal end 116 of inner shaft 114 is coupled to a first hub 150 having a proximal port 152 with a hemostatic valve. In an embodiment, lumen 120 may be sized to slidingly accommodate a guidewire 156 so that catheter assembly 100 is trackable over guidewire 156. Guidewire 156 is an elongate substantially straight tubular or cylindrical element that is configured to be slidably disposed within lumen 120 of inner shaft 114 and removable therefrom. Beyond distal end 118 of inner shaft 114, guidewire 156 extends through lumen 108 of outer shaft 102 such that the guidewire 156 extends through the entire length of the catheter assembly. In an embodiment, catheter assembly 100 may be sized to be used with a 6F introducer sheath with lumen 120 of inner shaft 114 being sized to accommodate a guidewire having an outer diameter of 0.035 inch. Alternatively, catheter assembly 100 may be sized to be used with a 5F introducer sheath with lumen 120 of inner shaft 114 being sized to accommodate a guidewire having an outer diameter of 0.018 inch. Although catheter assembly 100 is shown in FIG. 1 with a guidewire extending there-through, other elongated components such as but not limited to a needle component may extend through inner shaft 114. Inner shaft 114 may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded.

Support structure 130 is formed to have a shape memory to resume a shape set laterally expanded state as shown in FIG. 6B from a compressed state shown in FIG. 6A. More particularly, FIG. 6A illustrates a top view of distal end portion of inner shaft 114 with support structure 130 in a compressed state within outer shaft 102 (shown in phantom in FIG. 6A), while FIG. 6B illustrates a top view of the distal end portion of inner shaft 114 in which support structure 130 resumes its expanded state (with outer shaft 102 being removed from FIG. 6B for illustrative purposes). More particularly, in its shape set or relaxed condition, support structure 130 assumes the expanded state of FIG. 6B and therefore may be described as self-expanding. In the expanded state, support structure 130 includes first and second wings 136A, 136B having integral peaks or bends 138A, 138B, respectively, that bow laterally outward from inner shaft 114 in opposite directions from each other. As used herein, the term laterally refers to a direction along an axis transverse to longitudinal axis $L_A$ of catheter assembly 100. Each of first and second wings 136A, 136B is a longitudinally extending band that bridges a length between proximal and distal tube segments 132, 134, respectively, of support structure 130. Inner shaft 114 extends through the proximal and distal tube segments 132, 134 such that the longitudinally extending band that forms first wing 136A extends along a first side of inner shaft 114 and the longitudinally extending band that forms second wing 136B extends along an opposite, second side of inner shaft 114. In an embodiment, distal tube segment 134 is fixedly secured or attached to inner shaft 114 while proximal tube segment 132 is slidingly disposed over inner shaft 114. As such, while transforming from the compressed state of FIG. 6A to the laterally expanded state of FIG. 6B, proximal tube segment 132 slides or moves over inner shaft 114 towards distal tube segment 134 to permit first and second wings 136A, 136B to outwardly expand or deploy into the expanded state. While transforming back to the compressed state of FIG. 6A from the laterally expanded state of FIG. 6B, proximal tube segment 132 slides or moves over inner shaft 114 away from distal tube segment 134 to inwardly compress or collapse into the compressed state for retrieval. Alternatively, proximal tube segment 132 is fixedly secured or attached to inner shaft 114 while distal tube segment 134 is slidingly disposed over inner shaft 114.

As will be discussed in more detail herein, in order to control or dictate the shape of stabilization mechanism 122, support structure 130 is formed from a generally stiffer material than balloon 124 so that balloon 124 conforms to the shape of support structure 130. Suitable materials for self-expanding support structure 130 include but are not limited to shape memory materials such as nitinol, other super-elastic alloys, and shape-memory polymers. Self-expanding support structure 130 may also be formed from metallic materials such as stainless steel.

The proximal end 104 of outer shaft 102 extends out of the patient and is coupled to a second hub 140. Proximal end 104 of outer shaft 102 is disposed within a strain relief element 154 that is attached to distally extend from second hub 140. Second hub 140 includes a proximal port 144 with a hemostatic valve to accommodate insertion of other components of catheter assembly 100 into lumen 108 of outer shaft 102. An inflation shaft or tube 110 defining an inflation lumen 112 extends through lumen 108 of outer shaft 102 to allow inflation fluid received through a Luer fitting 142 of hub 140 to be delivered to balloon 124. It will be understood by one of ordinary skill in the art that Luer fitting 142, or some other type of fitting, may be connected to a source of inflation fluid (not shown) and may be of another construction or configuration without departing from the scope of the present invention. Other types of construction are also suitable for outer shaft 102, such as, without limitation thereto, a catheter shaft having a working lumen and an inflation lumen formed by multi-lumen profile extrusion. In another embodiment hereof, discussed in more detail with respect to the embodiment of FIGS. 9 and 10, the outer shaft may include an inflation shaft or tube that is attached to extend along an outer surface of the outer shaft to allow inflation fluid received through Luer fitting 142 of second hub 140 to be delivered to balloon 124.

In the embodiment of FIGS. 1-2, balloon 124 forms an integral distal portion of outer shaft 102. More particularly, outer shaft 102 may be considered to include a first or proximal portion 146, a second or distal tip portion 148, and balloon 124 disposed or sandwiched between proximal portion 146 and distal tip portion 148. Proximal portion 146, balloon 124, and distal tip portion 148 collectively define continuous lumen 108 of outer shaft 102. In accordance with embodiments hereof, proximal portion 146 is a tubular or cylindrical shaft segment having a first flexibility, distal tip portion 148 is a tubular or cylindrical shaft segment having a second flexibility, and balloon 124 is a tubular or cylindrical element having a third flexibility with balloon 124 being more flexible or compliant than proximal and distal tip portions 146, 148. In an embodiment, proximal portion 146 is an elongate polymeric tube having a reinforcement layer, distal tip portion 148 is a polymeric tube that is more flexible than the proximal portion, and balloon 124 is a cylindrical or tubular element formed of a compliant material in order to conform to the shape of support element 130. The inflated state of balloon 124 will be discussed in more detail herein with respect to deployment of stabilization mechanism 122. Balloon 124 has a proximal end 126 and a distal end 128, and ends 126, 128 may be welded or otherwise mechanically coupled to proximal and distal tip portions 146, 148 to form the continuous outer shaft. Suitable compliant materials for balloon 124 include but are not limited to polyether block amide, PEBAX® 5533, PEBAX® 4033, silicon, polyurethane, or polyether-based thermoplastic polyurethanes (TPUs) such as Tecothane or Tecoflex 90. The remaining portions of outer shaft 102, i.e., proximal portion 146 and distal tip portion 148, may be formed of semi-compliant or non-compliant polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded.

Sealing members 127, 129 are disposed internally of outer shaft 102, radially externally of inner shaft 114 and adjacent to proximal and distal balloon ends 126, 128, respectively, for preventing leakage of inflation fluid. Sealing members 127, 129 fill or close the annular space between outer shaft 102 and inner shaft 114, thereby sealing or preventing leakage of inflation fluid that is delivered to balloon 124 for expansion thereof. More particularly, inflation fluid is delivered to balloon 124 via inflation tube 110, which extends through a wall of proximal sealing member 127 and extends just beyond or distal to proximal end 126 of balloon 124 and sealing member 127. Sealing members 127, 129 are valve-like or wiper seals that allow sliding or longitudinal movement of inner shaft 114 within outer shaft 102 while preventing leakage of the inflation fluid used for inflating balloon 124. For examples, sealing members 127, 129 are commercially available from Merit Medical Systems, Inc. of South Jordan, Utah, Qosina Corp. of Edgewood, N.Y., or Minivalve International B.V. of Oldenzaal, Netherlands. Sealing members 127, 129 may be moulded, welded, coupled via adhesive, or otherwise attached to an inner surface of outer shaft 102 such that the sealing members are integral with the outer shaft.

Deployment of catheter assembly 100 and stabilization mechanism 122 will now be discussed in more detail with reference to FIGS. 1-2. FIG. 1 illustrates inner shaft 114 and stabilization mechanism 122 in a first or delivery configuration in which self-expanding support structure 130 is held in a compressed or constrained state since it is positioned within outer shaft 102 proximal of balloon 124, i.e., positioned within proximal portion 146 of outer shaft 102. As best shown in the top view of FIG. 6A, when in the compressed state, first and second wings 136A, 136B of support structure 130 are substantially straightened and extend parallel or in line with longitudinal axis $L_A$ of catheter assembly 100. Proximal tube segment 132 of support structure 130, which is disposed over inner shaft 114 but is not fixed thereto, is free to slide or move in a longitudinal (axial) direction over inner shaft 114 to permit first and second wings 136A, 136B to collapse or straighten within outer shaft 102 into the compressed state. Outer shaft 102 is thus being employed as an outer sheath, restraining self-expanding support element 130 therein and not permitting it to expand.

FIGS. 2 and 3 illustrate inner shaft 114 and stabilization mechanism 122 in a second or deployed configuration, with other components of the catheter system removed for illustrative purposes only. More particularly, when it is desired to deploy stabilization mechanism 122, outer shaft 102 and inner shaft 114 are moved relative to each other in order to longitudinally align or overlap support structure 130 and balloon 124. Outer shaft 102 may be proximally retracted relative to inner shaft 114; alternatively, inner shaft 114 may be distally advanced relative to outer shaft 102, or a combination of both. Once the two structures of the stabilization mechanism are longitudinally aligned, support structure 130 is no longer constrained by proximal portion 146 of outer shaft 102 and is thus permitted to return to its expanded or deployed state within balloon 124 as shown in FIGS. 2-3. Proximal tube segment 132 of support structure 130 slides or moves in a distal direction over inner shaft 114 to permit first and second wings 136A, 136B to outwardly expand or laterally bow into the deployed configuration. When wings 136A, 136B deploy, the compliant material of balloon 124 is laterally pushed or extended outward by peaks or bends 138A, 138B of wings 136A, 136B such that the balloon is stretched over the expanded support structure. Laterally expanded support structure 130 pushes or forces compliant balloon 124 outward in opposing directions from the longitudinal axis $L_A$ of catheter assembly 100, as shown in FIG. 3.

After support structure 130 is laterally expanded within balloon 124, balloon 124 is then inflated at a low pressure, e.g. in the range from about 2 and 5 bar. As previously stated, balloon 124 has a cylindrical or tubular profile, and thus without support structure 130 positioned therein, cylindrical balloon 124 would inflate to a substantially cylindrical shape having a circular cross-section as shown in FIG. 2B. However, when balloon 124 is inflated with low pressure over laterally expanded support structure 130, compliant balloon 124 is stretched laterally outward and the expansion of balloon 124 is constrained or limited by the laterally expanded support structure 130 therein from obtaining a circular cross-section and a cylindrical shape. Stated another way, balloon 124 may be considered to have a flattened or pancake-like shape since radial expansion thereof is constrained by the expanded support structure therein. More particularly, during inflation, balloon 124 sits or abuts against laterally expanded support structure 130 so that, in the inflated state, balloon 124 remains in contact with or is only slightly spaced apart from the lateral-most or outermost surfaces of the laterally expanded support structure 130 along the length of the balloon. Accordingly, when in the inflated state, balloon 124 matches or corresponds to the geometry or bowed shape of laterally expanded support structure 130 positioned within the interior of balloon 124 and the cross-sectional size and/or shape of inflated balloon 124 varies along its length in accordance with the bowed support structure. When self-expanding support structure 130 is expanded and the balloon 124 is inflated, the balloon has a flattened, non-circular cross-section as best shown in the cross-sectional view of FIG. 2A. As used herein, flattened, non-circular cross-section includes oval, egg-shaped, elliptical, or other generally rounded oblong shapes that resemble a rectangle with opposing curved or semicircular ends. Particularly, as shown in FIG. 2A, the width dimension W of stabilization mechanism 122 is greater than the height dimension H of stabilization mechanism 122 and opposing ends 123A, 123B are generally rounded.

When inflated around the expanded support structure 130, balloon 124 is atraumatic and expands into contact with the surrounding patient's anatomy to fill out or occupy the target anatomical space to improve anchoring as well as minimize damage to the surrounding anatomy since it is the balloon that comes into contact with the vessel wall and not the metallic wings of the support structure 130. Balloon 124 serves to provide stabilization mechanism 122 with a smooth, rounded and stable profile while maintaining the laterally extended shape of expanded support structure 130. Stated another way, laterally expanded support structure 130 dictates the overall flattened or pancake-like shape or profile of inflated balloon 124, as well as the overall lateral and longitudinally-extending shape or profile of stabilization mechanism 122. As used herein, "profile" refers to a shape of the balloon or stabilization mechanism in a top view as seen in FIG. 2A and FIG. 3. In the second or deployed configuration, stabilization mechanism 122 has a lateral and longitudinally-extending profile that resembles a diamond or a manta-ray having opposing triangular portions extending along the length thereof, which are formed or produced by bowed wings 136A, 136B of the expanded support structure.

Figure 4:
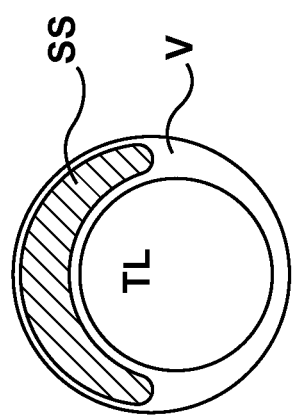
FIG. 4 is an illustration of a subintimal space of a vessel.

When positioned in target anatomy such as a subintimal space, stabilization mechanism 122 conforms to the shape of the native anatomy due to the flexible and/or compliant material characteristics thereof. The flattened, laterally-extending profile is required to conform to the shape of the target anatomical space while avoiding over-expansion of the patient's anatomy. More particularly, FIG. 4 illustrates a cross-sectional view of a vessel V having a true lumen TL and a subintimal space SS. As shown, subintimal space SS may be described as having an arc, curve, or C shape. FIG. 5 illustrates stabilization mechanism 122 deployed within subintimal space SS of vessel V. When disposed within subintimal space SS and subjected to a bending load or force via the native anatomy, stabilization mechanism 122 conforms to the curved shape of the subintimal space due to the flexible and compliant characteristics of the materials thereof. As shown, when deployed within subintimal space SS, the flattened, laterally-extending profile of the stabilization mechanism is shaped into an arc, curve, or C shape. Deployed wings 136A, 136B of support structure 130 bend or curve with the native anatomy. Thus, the flattened, laterally-extending profile improves anchoring of stabilization mechanism 122 within target anatomical space because stabilization mechanism 122 may adapt its shape to the subintimal space geometry, and thereby avoid over-expansion of the patient's anatomy.

Once anchoring within the target anatomy is no longer desired, stabilization mechanism 122 may be retrieved for storage and subsequent use, or for removal of catheter assembly 100. When it is desired to retrieve stabilization mechanism 122, balloon 124 is deflated and then outer shaft 102 and inner shaft 114 are moved relative to each other in order to return support structure 130 to the position of FIG. 1 in which support structure 130 is constrained or compressed by proximal portion 146 of outer shaft 102. More particularly, outer shaft 102 may be distally advanced relative to inner shaft 114; alternatively inner shaft 114 may be proximally retracted relative to outer shaft 102, or a combination of both. During relative movement between outer shaft 102 and inner shaft 114, proximal tube segment 132 of support structure 130 slides or moves in a proximal direction over inner shaft 114 to permit first and second wings 136A, 136B to collapse or straighten into their compressed state. Although not required, in another embodiment hereof (not shown), catheter assembly 100 may include additional elements to assist in the retrieval of support element 130, including but not limited to an additional outer sheath that may be distally advanced thereover to forcibly collapse wings 136A, 136B and/or an intermediate shaft or tether that is attached to proximal tube segment 132 of support structure 130 that may be pulled proximally to collapse wings 136A, 136B.

As previously explained, due to the material thereof, support structure 130 is sufficiently compliant or flexible to conform to the shape of the target anatomical space after deployment. However, in addition to exploiting the material properties of the support structure, the support structure may also include thinned or weakened areas or joints that increase flexibility of the support structure wings at predetermined locations. For example, with respect to FIGS. 7 and 8, a catheter assembly 700 includes a stabilization mechanism 722 having a support structure 730 mounted on an inner shaft 714 and a balloon 724 mounted on an outer shaft (not shown) similar to stabilization mechanism 122 above. In this embodiment, however, wings 736A, 736B include multiple thinned or weakened areas or joints 739 that permit selective bending of the wings at predetermined locations. When disposed within subintimal space SS and subjected to a bending load or force via the native anatomy, stabilization mechanism 722 conforms to the curved shape of the subintimal space due to the thinned or weakened areas or joints 739 of support structure 730. The cross-sectional width of wings 736A, 736B at joints 739 are smaller or lower than the width of the wings along the remaining lengths thereof. Thinned or weakened areas or joints 739 improve bending or curving of wings 736A, 736B with the native anatomy.

FIGS. 9 and 10 illustrate a distal portion of a catheter assembly 900 according to another embodiment hereof. Similar to catheter assembly 100, catheter assembly 900 includes a stabilization mechanism 922 for stabilizing or anchoring the catheter assembly within a subintimal space. An inflatable balloon 924 of the stabilization mechanism is shown in phantom in FIGS. 9-10 so that the components internal thereto are clearly shown. Stabilization mechanism 922 includes a self-expanding support structure 930 that is slidably positionable within inflatable balloon 924. More particularly, catheter assembly 900 includes an outer shaft 902 including inflatable balloon 924 mounted on a distal portion thereof and an inner shaft 914 including self-expanding support structure 930 having deployable wings 936A, 936B mounted on a distal end thereof. Inner shaft 914 is slidably disposed within a lumen (not shown in FIG. 9) of outer shaft 902, and support structure 930 is mounted over inner shaft 914 as described above with respect to support structure 130 and inner shaft 114. However, in this embodiment, outer shaft 902 is a single or continuous tubular shaft and balloon 924 is mounted over a distal portion thereof. Within balloon 924, outer shaft 902 includes corresponding openings or windows 960 formed through a sidewall thereof which allow deployment and outward, lateral expansion of wings 936A, 936B. When it is desired to deploy stabilization mechanism 922, outer shaft 902 and inner shaft 914 are moved relative to each other in order to longitudinally align wings 936A, 936B with openings 960. Once wings 936A, 936B and openings 960 are longitudinally aligned, support structure 930 is no longer constrained by outer sheath 902 and is thus permitted to return to its expanded or deployed state within balloon 924 as shown in FIG. 9. Similar to support structure 130, proximal tube segment 932 of support structure 930 is slidably disposed over inner shaft 914, and thus is permitted to slide or move in a distal direction over inner shaft 914 towards distal tube segment 934 to permit wings 936A, 936B to outwardly expand or laterally bow into the deployed configuration. Thus, rather than longitudinally aligning support structure 130 with compliant balloon 124 to permit self-expansion as described in the embodiment above, wings 936A, 936B of support structure 930 must be longitudinally aligned with openings or windows 960 of outer shaft 902 to permit self-expansion thereof. Openings or windows 960 provide controlled deployment and assist in retrieval or collapse of wings 936A, 936B because the openings reduce the force required for movement of wings 936A, 936B of support structure 930.

In addition to openings 960, catheter assembly 900 also illustrates another embodiment of the inflation lumen. More particularly, as best shown in the enlarged perspective view of FIG. 10, outer shaft 902 includes an inflation shaft or tube 910 defining a lumen 912 that is attached to extend along an outer surface of outer shaft 902 to allow inflation fluid received through a proximal hub (not shown) to be delivered to balloon 924. In an embodiment hereof, when inflation tube 910 is external to outer shaft 902, an outer sheath 958 (shown in phantom in FIG. 9 so that the components internal thereto are clearly shown) may be disposed over the inflation tube and outer shaft in order to couple the inflation tube to the outer shaft. However, outer sheath 958 is optional and the external inflation tube may be coupled to the outer shaft using other coupling mechanisms or methodologies known in the art. Sealing members 927, 929 are disposed internally to outer shaft 902, radially external to inner shaft 914 and adjacent to proximal and distal balloon ends 926, 928, respectively, for preventing leakage of inflation fluid. Inflation tube 910 extends from the proximal hub into balloon 924, such that a distal end or port 911 of inflation tube 910 is positioned or extends just beyond or distal to proximal end 926 of balloon 924 and sealing member 927. Similar to sealing members 127, 129, sealing members 927, 929 are valve-like or wiper seals that allow sliding or longitudinal movement of internal shaft 914 within outer shaft 902 while preventing leakage of the inflation fluid used for inflating balloon 924.

FIGS. 11 and 12 illustrate a distal portion of a catheter assembly 1100 having a stabilization mechanism 1122 in first and second configurations, respectively, according to another embodiment hereof. An inflatable balloon 1124 of the stabilization mechanism is shown in phantom in FIGS. 11-12 so that the components internal thereto are clearly shown. Catheter assembly 1100 is similar to catheter assembly 1200 in that outer shaft 1102 includes windows or openings 1160 for deployment of wings 1136A, 1136B of support structure 1130. Support structure 1130 is similar in structure to support structure 130, with one of the proximal and distal tube segments (not shown in FIG. 11) being slidingly disposed over inner shaft 1114 and the other one of the proximal and distal tube segments (not shown in FIG. 11) being fixed or secured to inner shaft 1114 to permit wings 1136A, 1136B to outwardly expand or laterally bow into the deployed configuration. In this embodiment, deployment of wings 1136A, 1136B is achieved via relative rotation between inner shaft 1114 and outer shaft 1102 rather than relative longitudinal movement thereof. Inner shaft 1114 is not slidingly disposed relative to outer shaft 1102 but rather is rotatably disposed relative to outer shaft 1102 so deployment is achieved when wings 1136A, 1136B of support structure 1130 circumferentially align with windows or openings 1160. Rotation is illustrated via a directional arrow 1262 in FIG. 12. Once wings 1136A, 1136B and openings 1160 are circumferentially aligned, wings 1136A, 1136B outwardly expand or laterally bow into their expanded state through openings 960 as shown in FIG. 12. Sealing members 1127, 1129 are disposed internally to outer shaft 1102, radially external to inner shaft 1114 and adjacent to proximal and distal balloon ends 1126, 1128, respectively, for preventing leakage of inflation fluid. Similar to sealing members 127, 129, sealing members 1127, 1129 are valve-like or wiper seals that allow rotational movement of internal shaft 1114 within outer shaft 1102 while preventing leakage of the inflation fluid used for inflating balloon 1124.

Figure 13:
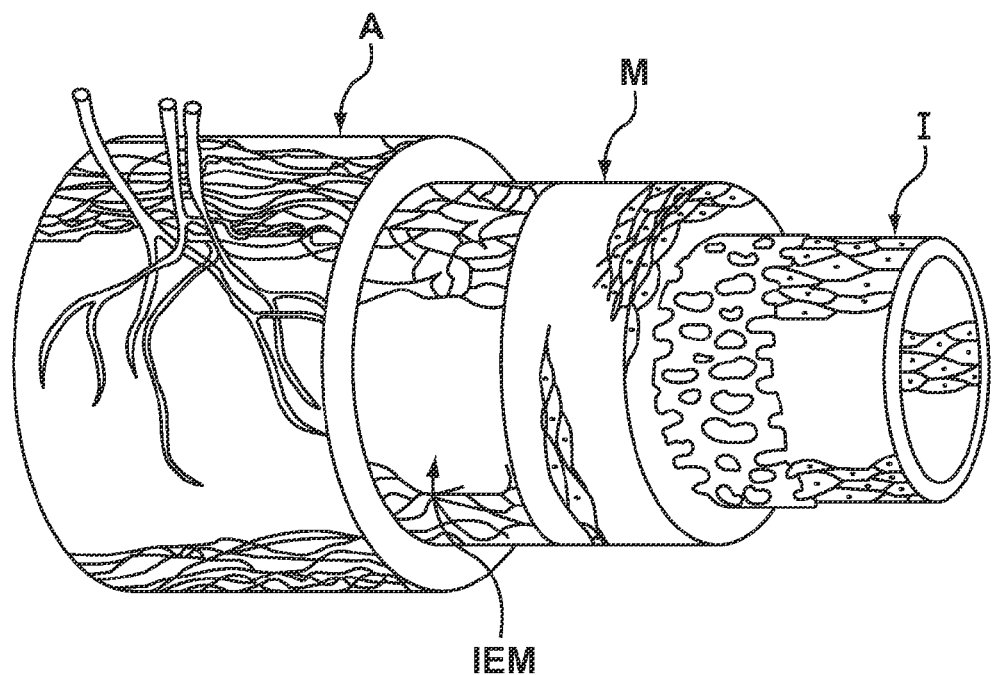
FIG. 13 is a diagram of an artery showing the three layers of tissue that comprise the artery wall.

As previously mentioned, catheter assemblies according to embodiments hereof may be utilized in a method for re-entering the true lumen of a vessel after subintimally bypassing an occlusion in a blood vessel such as a chronic total occlusion (CTO) of an artery. FIG. 13 is a sectional view of the anatomy of an artery wall, which for purposes of this description is shown to consist essentially of three layers, the tunica intima I ("intima"), tunica media M ("media") which is the thickest layer of the wall, and the tunica adventitia A ("adventitia"). In some arteries an internal elastic membrane IEM is disposed between the media M and adventitia A. The adventitia A is made of collagen, vasa vasorum and nerve cells, the media M is made of smooth muscle cells, and the intima I is made up of a single layer of endothelial cells that provide a nonthrombogenic surface for flowing blood. A catheter assembly in accordance with embodiments hereof is used as part of a system for creating a subintimal reentry conduit within a wall of a blood vessel V to allow blood flow around an occlusion. FIGS. 14-24 illustrate an exemplary method of using the above-described catheter assembly 100 to bypass a chronic total occlusion (CTO) according to an embodiment hereof, but it would be understood by one of ordinary skill in the art that the depicted method may be adapted to be performed by other catheter assembly disclosed herein. Although described in relation to bypassing a CTO, it should be understood that the methods and apparatus described herein may be used for bypassing any tight stenoses in arteries or other anatomical conduits and are not limited to total occlusions.

Figure 14:
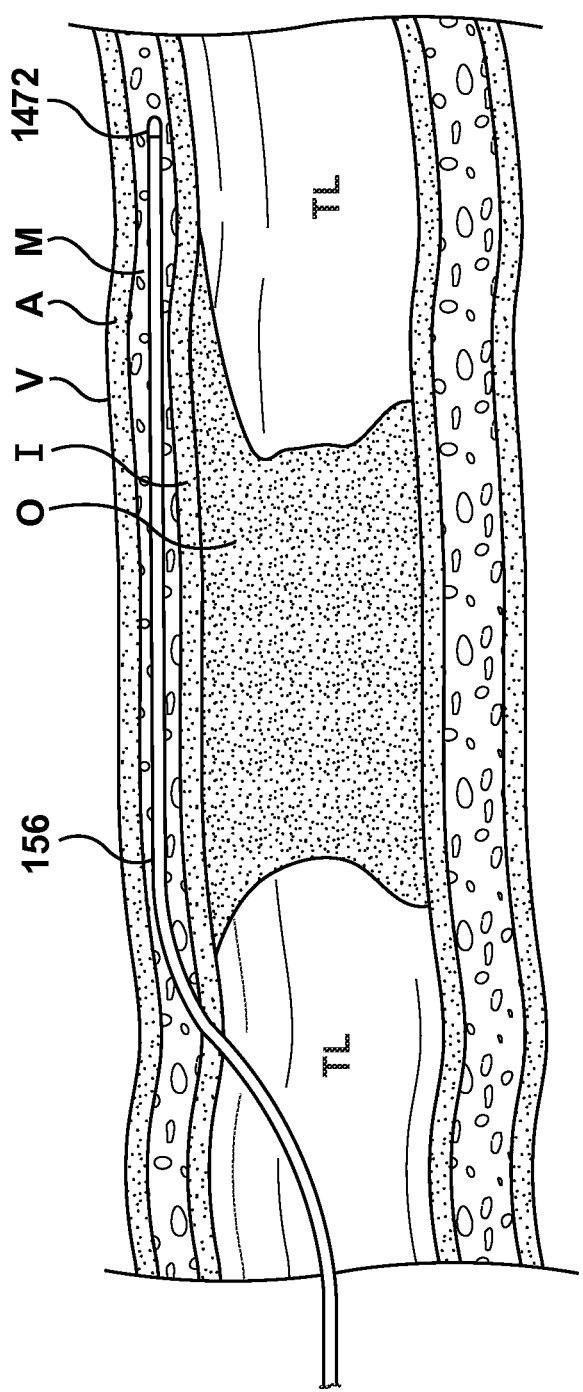

As shown in FIG. 14, in accordance with techniques known in the field of interventional cardiology and/or interventional radiology, guidewire 156 having a distal end 1472 is transluminally advanced through the vasculature to a position upstream or proximal of a treatment site, which in this instance is shown as occlusion O within a true lumen TL of blood vessel V. Guidewire 156 pierces the intima I and is advanced distally to create a subintimal space by locally dissecting or delaminating intima I from media M or by burrowing through media M. Guidewire 156 has a relatively larger outer diameter such as between 0.032-0.040 inches in order to have sufficient column strength to gain access to the subintimal space of vessel V. In order to pierce the intima I, a clinician may manipulate distal end 1472 of guidewire 156 by prolapsing or bending-over the distal end of guidewire 156 (not shown) and thereafter may use the stiffer arc or loop of the prolapsed distal end to pierce into the intima I to advance guidewire 156 there through. The piercing of the intima I is aided by the fact that typically blood vessel V is diseased, which in some instances makes the intima I prone to piercing. Guidewire 156 is distally advanced within the subintimal space from a near or proximal side of occlusion O to a position where distal end 1472 thereof is positioned in the subintimal tract on a far or distal side of occlusion O.

Alternatively, another device other than guidewire 156 may be initially used to create the subintimal tract. Those of ordinary skill in the art will appreciate and understand the types of alternative devices that may be used in this step including an apparatus known as an "olive", a laser wire, an elongate radiofrequency electrode, a microcatheter, or any other device suitable for boring or advancing through the vessel tissue. If an alternative device is used instead of guidewire 156 to form the subintimal tract, such alternative device may be removed and replaced with guidewire 156 or a smaller diameter guidewire after the subintimal tract has been formed.

Figure 15:
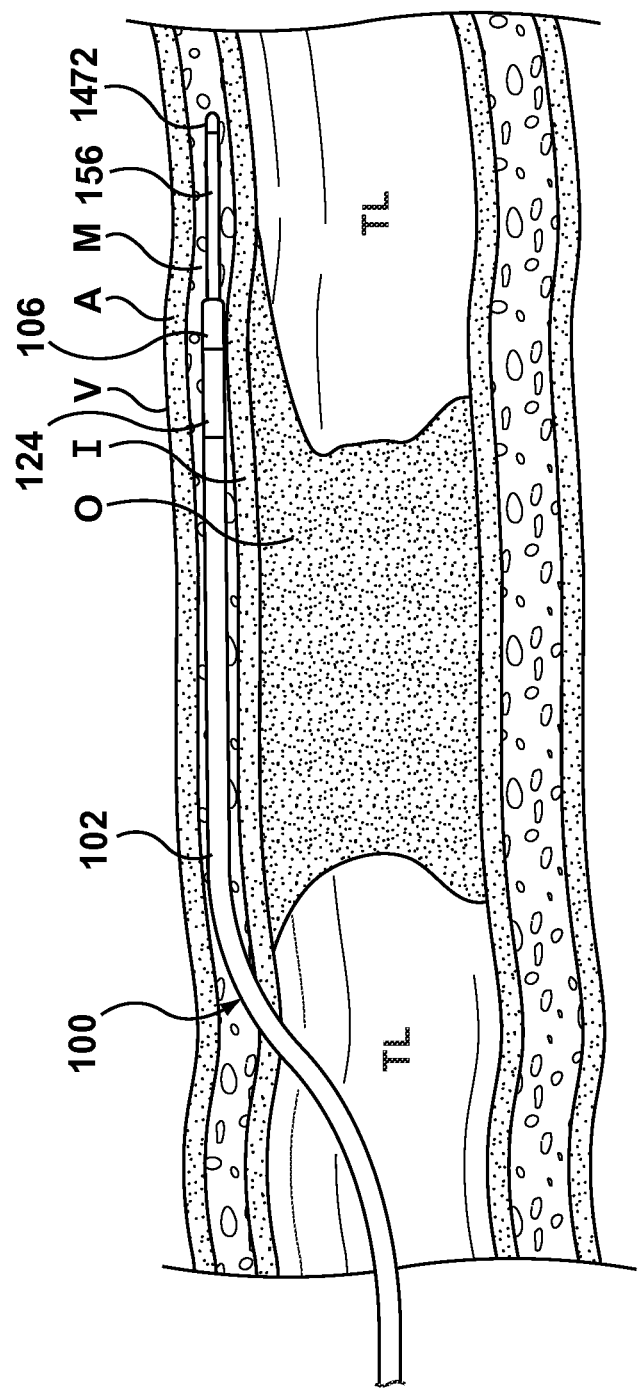

After the subintimal space or tract is formed, catheter assembly 100 is tracked over guidewire 156 and advanced until distal end 106 of outer shaft 102 is disposed at the far end of occlusion O as shown in FIG. 15. During the step of tracking catheter assembly 100, self-expanding support structure 130 is held in a radially compressed state within the outer shaft 102 that is proximal of balloon 124. Once catheter assembly 100 is positioned as desired within the subintimal space, self-expanding support structure 130 is moved or positioned within balloon 124 of the catheter assembly, thereby permitting support structure 130 to self-expand and return to an expanded or deployed state within the balloon as shown in FIGS. 16 and 16A. More particularly, during the step of positioning, outer shaft 102 is proximally retracted relative to inner shaft 114 until self-expanding support structure 130 slides within balloon 124 to be longitudinally aligned or overlapping therewith. As best shown in FIG. 16A, the compliant material of balloon 124 is laterally pushed or extended outward such that the balloon is stretched over the deployed wings 136A, 136B of support structure 130.

Balloon 124 is then inflated around support structure 130, as shown in FIGS. 17 and 17A. With inflation of balloon 124, stabilization mechanism 122 is thereby deployed and catheter assembly 100 is anchored within the subintimal tract. Balloon 124 is inflated at a low pressure regime so that inflated balloon 124 matches or corresponds to the geometry or profile of expanded support structure 130 therein. As shown in FIG. 17A, when inflated around the expanded support structure 130, balloon 124 expands into contact with the surrounding patient's anatomy to fill out or occupy the target anatomical space to improve anchoring, to provide stabilization mechanism 122 with a smooth, rounded-out, and stable profile, and to minimize damage to the surrounding anatomy.

Figure 18:
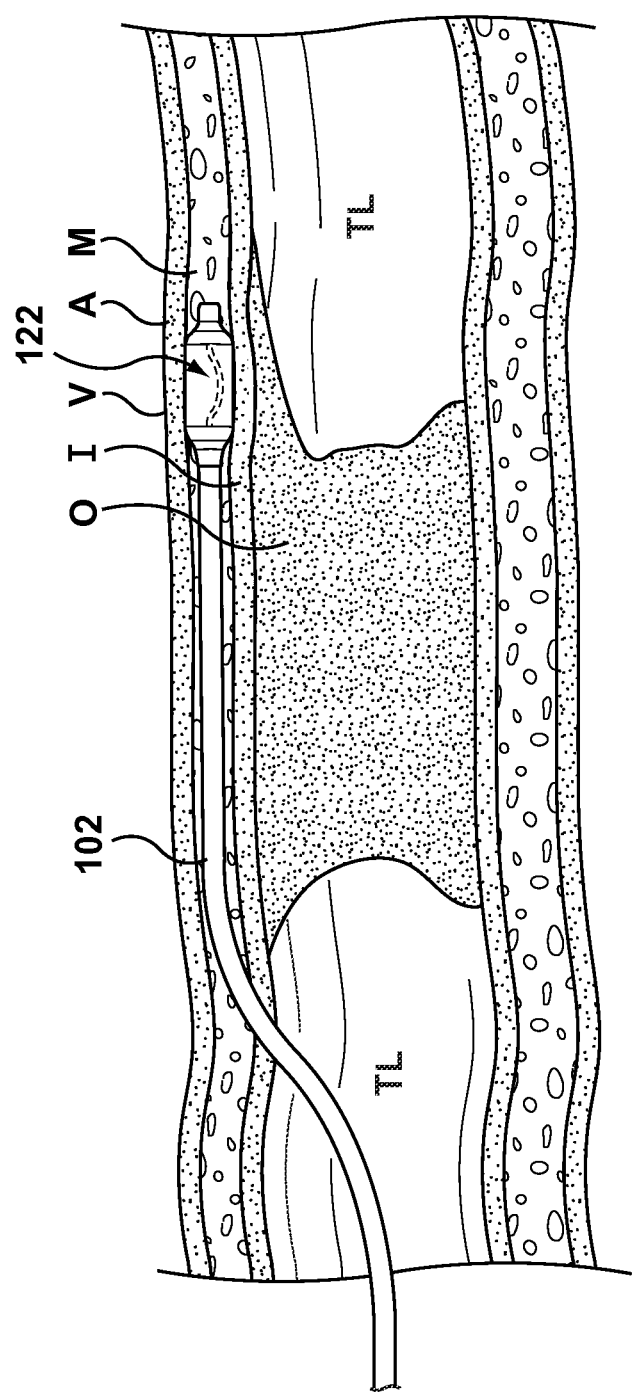

Guidewire 156 may then be proximally retracted and removed, with stabilization mechanism 122 of catheter 100 deployed as shown in FIG. 18. In order to bypass the CTO, a needle component 1974 having a pre-formed or angled distal tip segment 1976 is advanced or loaded into lumen 120 of inner shaft 114. A side view of needle 1974 is shown in FIG. 19A. Needle component 1974 is an elongate tubular or cylindrical element that is configured to be slidably disposed within lumen 120 of inner shaft 114 and removable therefrom. Needle component 1974 has an elongated straight proximal segment 1975 and angled distal tip segment 1976, with a distal end 1978 that includes a distal tip 1980 configured to pierce or penetrate through a wall of a vessel. Pre-formed angled distal tip segment 1976 extends, bends, or otherwise curves at an acute angle Θ relative to the longitudinal axis of elongated proximal segment 1975. In embodiments hereof, angle Θ may be in the range of 30° to 80°. In an embodiment at least angled distal tip segment 1976 of needle component 1974 is formed from a biocompatible resilient metal such as spring temper stainless steel or nitinol, which utilizes the elastic properties of stress induced martensite, such that a heat or thermal treatment of the selected material may be used to set the shape memory of angled distal tip segment 1976. In an embodiment, needle component 1974 may be formed from more than one material, for e.g., with an elongated proximal segment 1975 being formed of stainless steel and only angled distal tip segment 1976 being formed of nitinol. Suitable materials for needle 1974 include but are not limited to nitinol, stainless steel, or relatively hard polymeric materials such as polyetheretherketone (PEEK).

During advancement or loading of needle component 1974 through inner shaft 114, angled distal tip segment 1976 of needle component 1974 is restrained or held in a straightened state within catheter assembly 100. The combination of the inner and outer shafts of catheter assembly 100 provide sufficient rigidity to maintain angled distal tip segment 1976 of needle component 1974 in a straightened state during loading and advancement thereof. When released from catheter assembly 100, angled distal tip segment 1976 resumes its shape memory geometry by its own internal restoring forces. Thus, needle component 1974 is advanced within inner shaft 114 until angled distal tip segment 1976 extends from or protrudes out of the distal end of outer shaft 102. The distal tip segment 1976 of needle component 1974 is then oriented such that subsequent distal advancement relative to catheter assembly 100 will cause the distal tip 1980 to penetrate through the intima and thereafter gain access to the true lumen of the vessel distal to, i.e., downstream of, the CTO as shown in FIG. 19.

Figure 20:
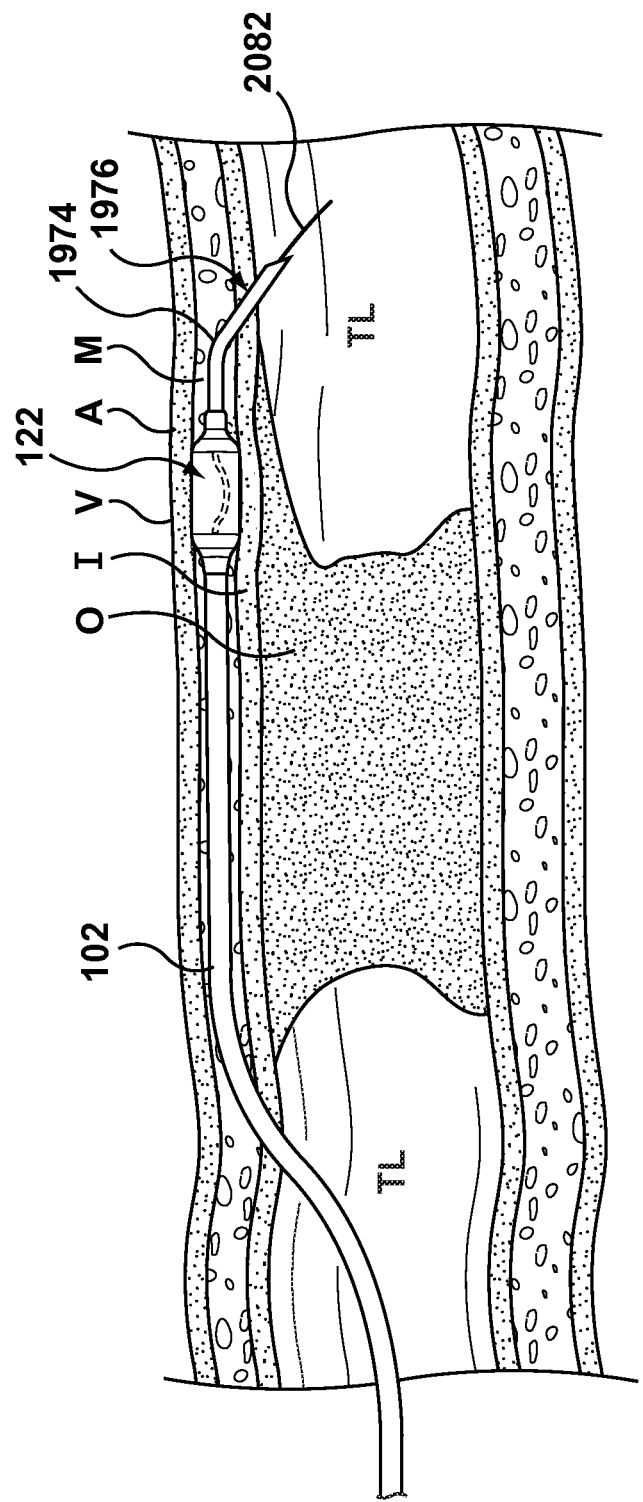
Figure 21:
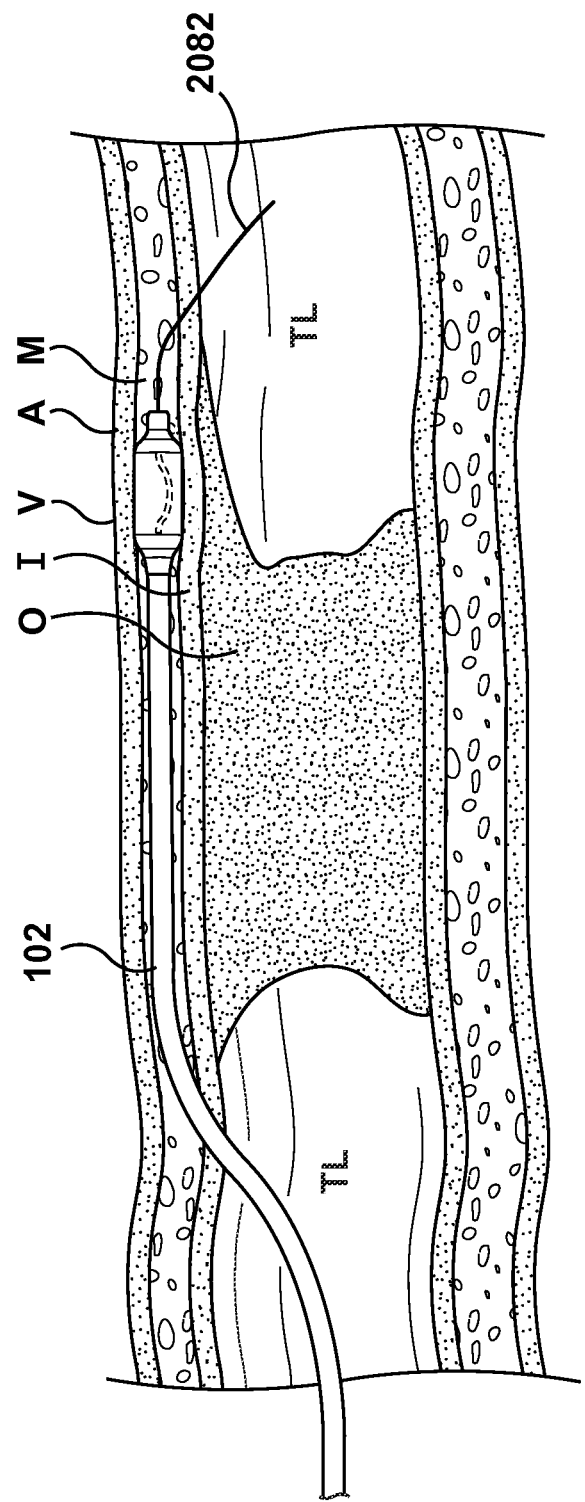

A second guidewire 2082 may be advanced through a lumen (not shown) of needle component 1974 and into the true lumen TL of vessel V as shown in FIG. 20. Guidewire 2082 has a relatively smaller outer diameter such as 0.014 inches in order to minimize the size of needle component 1974 and subsequently minimize the size of catheter assembly 100. With guidewire 2082 in place, needle component 1974 may be retracted and removed as shown in FIG. 21.

Figure 22:
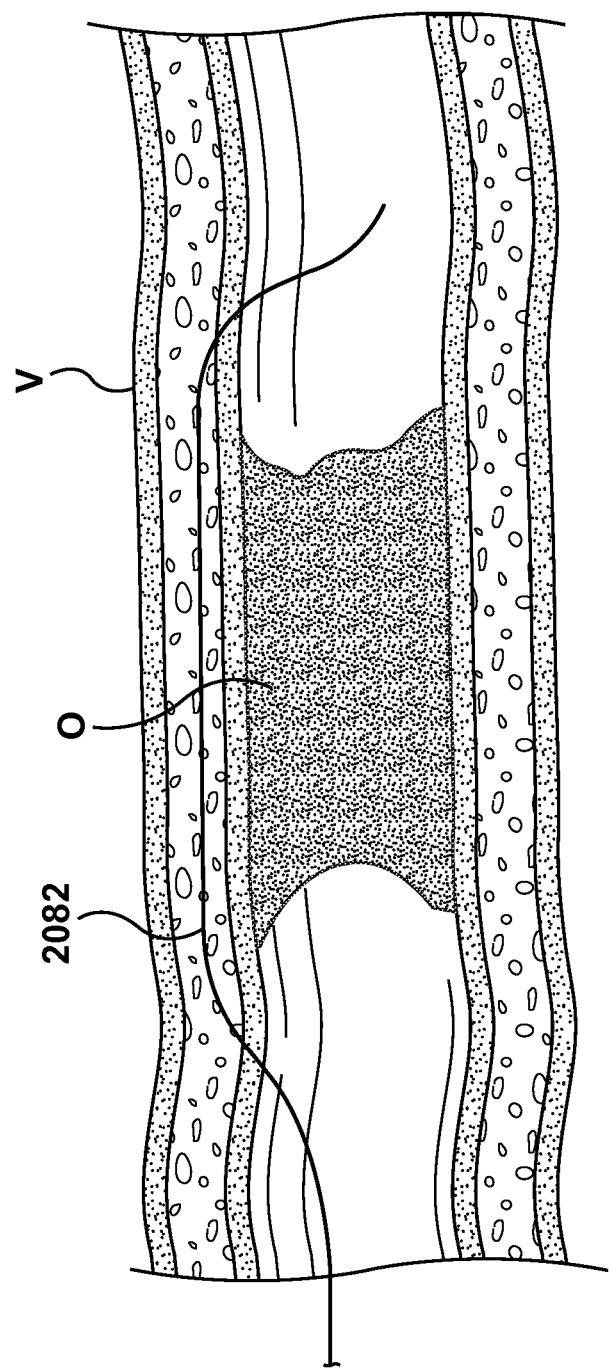
Figure 23:
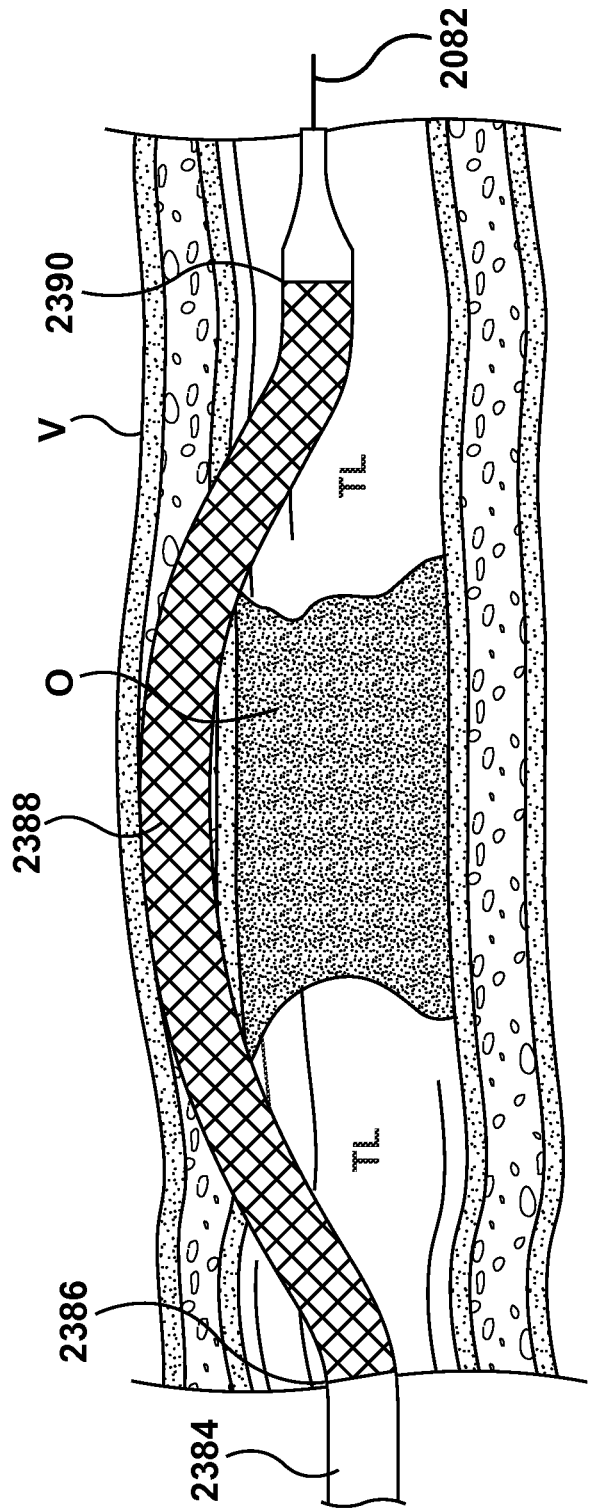
Figure 24:
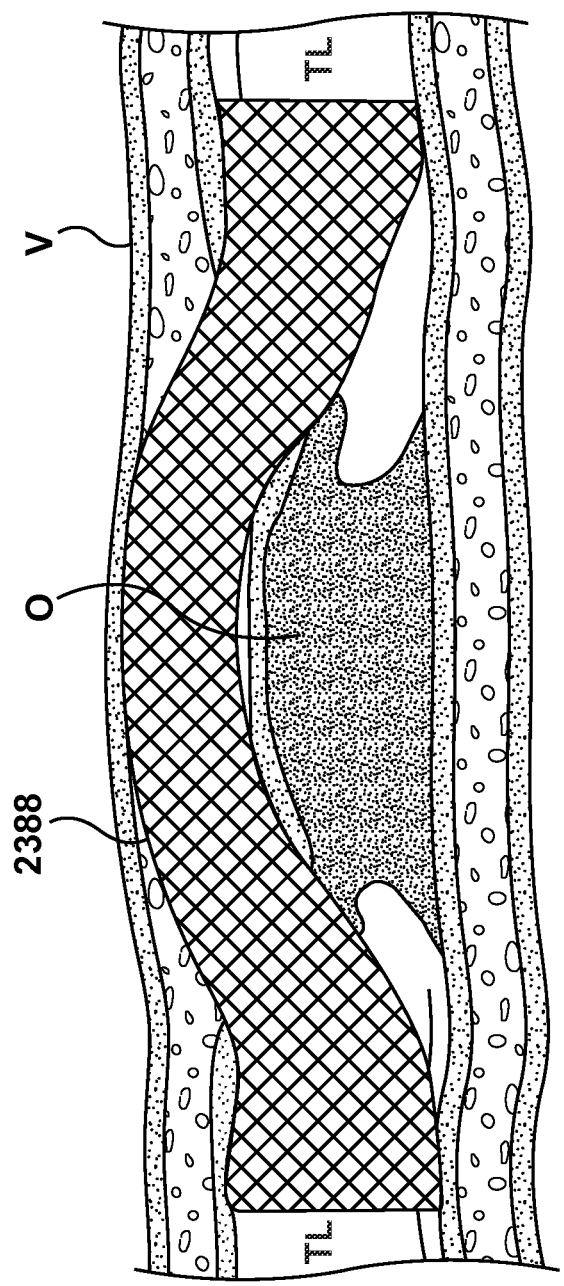

In one embodiment, at this stage of bypassing a CTO, catheter assembly 100 may be removed and guidewire 2082 may be left in place as shown in FIG. 22, such that guidewire 2082 extends in true lumen TL proximal to the CTO, through the subintimal tract, and back into true lumen TL distal to the CTO to enable the CTO to be successfully crossed via the subintimal conduit thus created. A covered or uncovered stent may be delivered over guidewire 2082 and implanted within the subintimal tract to facilitate flow from the lumen of the vessel upstream of the CTO, through the subintimal tract and back into the lumen of the vessel downstream of the CTO. For example, FIG. 23 shows a distal end of a catheter 2384 having a stent 2388 mounted thereon being advanced over guidewire 2082 to a position where a distal end 2390 of the radially collapsed stent 2388 is in true lumen TL of vessel V downstream of chronic total occlusion CTO, a proximal end 2386 of stent 2388 is in true lumen TL of vessel V upstream of chronic total occlusion CTO, and a tubular body of stent 2388 extends through the subintimal tract. Stent 2388 is then deployed (see FIG. 24) by either self-expansion or balloon inflation within the subintimal reentry conduit to dilate the subintimal tract and compress the adjacent chronic total occlusion CTO. Stent 2388 provides a scaffold which maintains the subintimal tract in an open condition capable of carrying blood downstream of chronic total occlusion CTO. Thereafter, guidewire 2082 and catheter 2384 may be removed from the patient, leaving stent 2388 in an expanded configuration and creating a radially supported, subintimal blood flow channel around chronic total occlusion CTO as seen in FIG. 24.

As described herein with respect to FIG. 19, needle component 1974 having a pre-formed or angled distal tip segment 1976 is advanced or loaded into lumen 120 of inner shaft 114 in order to bypass the CTO. In another embodiment hereof, as would be understood by one of ordinary skill in the art, the catheter assembly may be modified to include a side or exit port (not shown) through the outer shaft, proximal to the distal end of the outer shaft, in order to extend a needle or stylet through the intima and thereafter gain access to the true lumen of the vessel distal to, i.e., downstream of, the CTO. In addition, as would be understood by one of ordinary skill in the art, the catheter assembly may be modified to include a ramp or inclined surface (not shown) adjacent to the side or exit port to accomplish and/or supplement the desired angled extension of the needle or stylet from the catheter assembly.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, catheter assemblies according to embodiments hereof may include a feature to limit or restrict the amount of relative longitudinal movement between the inner and outer shafts for properly positioning the support structure in the balloon. For example, a safe lock mechanism may be incorporated into a proximal handle of the device that controls the movement or sliding of the inner shaft relative to the outer shaft. In addition, stabilization mechanisms described herein may be utilized to anchor catheter assemblies within a subintimal space without inflation of the balloon. Rather, the balloon may function as an outer member that surrounds the self-expanding support structure to minimize damage to the anatomy. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A catheter assembly comprising:
an outer shaft including an inflatable balloon having an inflated state and an uninflated state being disposed at a distal end thereof, wherein the inflatable balloon is an integral portion of the outer shaft with a proximal end of the balloon being coupled to a proximal portion of the outer shaft and a distal end of the balloon being coupled to a distal tip portion of the outer shaft; and
an inner shaft including a self-expanding support structure mounted on a distal portion thereof, the inner shaft being disposed within a lumen of the outer shaft such that the inner shaft is movable relative to the outer shaft, wherein in a first configuration the support structure is held in a compressed state within the outer shaft and in a second configuration the support structure is permitted to return to an expanded state within the inflatable balloon in the uninflated state,
wherein the inflatable balloon in the inflated state has a flattened laterally-extending profile dictated by the support structure in the expanded state contained therein, and
wherein together the inflated balloon and the expanded support structure are configured for stabilizing the catheter assembly within a subintimal space.

2. The catheter assembly of claim 1, wherein the support structure includes first and second wings that bow outward from the inner shaft in opposite directions from each other when in the expanded state.

3. The catheter assembly of claim 2, wherein the flattened laterally-extending profile of the balloon includes opposing triangular portions extending along the length thereof that are formed by the first and second wings of the support structure.

4. The catheter assembly of claim 2, wherein each of the first and second wings of the support structure is a longitudinally extending band that bridges a length between proximal and distal tube segments of the support structure and wherein the inner shaft extends through the proximal and distal tube segments of the support structure such that the longitudinally extending band that forms the first wing extends along a first side of the inner shaft and the longitudinally extending band that forms the second wing extends along an opposite, second side of the inner shaft.

5. The catheter assembly of claim 4, wherein each of the first and second wings of the support structure include at least one joint formed thereon to permit selective bending, the joint having a thinner cross-section than the remaining length of the band.

6. The catheter assembly of claim 1, wherein the proximal portion of the outer shaft, the distal tip portion of the outer shaft, and the balloon define a continuous lumen therethrough.

7. A catheter assembly comprising:
an outer shaft including an inflatable balloon disposed at a distal end thereof;
an inner shaft including a self-expanding support structure mounted on a distal end thereof, the inner shaft being disposed within a lumen of the outer shaft such that the inner shaft is movable relative to the outer shaft, wherein in a first configuration the support structure is held in a compressed state within the outer shaft and in a second configuration the support structure is permitted to return to an expanded state within the inflatable balloon such that the inflatable balloon has a flattened laterally-extending profile dictated by the support structure in the expanded state for stabilizing the catheter assembly within a subintimal space catheter assembly, wherein the outer shaft includes at least one opening formed through a sidewall thereof to permit the support structure to return to an expanded state.

8. A catheter assembly that provides stabilization within a subintimal space comprising:
a stabilization mechanism disposed at a distal end of the catheter assembly for anchoring the catheter assembly within the subintimal space, the stabilization mechanism including
a balloon having an uninflated state, the balloon being formed to have a substantially cylindrical shape with a circular cross-section in an inflated state, and a self-expanding support structure that is positionable within the balloon, the support structure having a flattened laterally-extending profile in an expanded state, wherein when the support structure in the expanded state is positioned within the balloon in the uninflated state, the support structure causes the balloon in the inflated state to have a flattened laterally-extending profile that corresponds to the flattened laterally-extending profile of the support structure.

9. The catheter assembly of claim 8, further comprising:

an elongate outer tubular component having an elongate inner tubular component slidably disposed therein, wherein the balloon is disposed at a distal end of the outer tubular component and the self-expanding support structure is mounted on a distal portion of the inner tubular component.

10. The catheter assembly of claim 9, wherein the self-expanding support structure is held in a radially compressed state when positioned within the outer tubular component proximal of the balloon.

11. The catheter assembly of claim 9, wherein the self-expanding support structure includes first and second wings that bow outward from the inner tubular component in opposite directions from each other when in the expanded state.

12. The catheter assembly of claim 11, wherein each of the first and second wings is a longitudinally extending band that bridges a length between proximal and distal tube segments of the self-expanding support structure and wherein the inner tubular component extends through the proximal and distal tube segments of the self-expanding support structure such that the longitudinally extending band that forms the first wing extends along a first side of the inner tubular component and the longitudinally extending band that forms the second wing extends along an opposite, second side of the inner tubular component.

13. The catheter assembly of claim 9, wherein the outer tubular component includes at least one opening formed through a sidewall thereof to permit the support structure to return to an expanded state.

14. The catheter assembly of claim 9, wherein the inflatable balloon is an integral portion of the outer tubular component, with a proximal end of the balloon being coupled to a proximal portion of the outer tubular component and a distal tip of the balloon being coupled to a distal tip portion of the outer tubular component, and the proximal portion, balloon, and distal tip portions define a continuous lumen there-through.

* * * * *